United States Patent [19]

Juraszyk et al.

[11] Patent Number: 4,766,213
[45] Date of Patent: Aug. 23, 1988

[54] 1,4-DIHYDROPYRIDINES

[75] Inventors: Horst Juraszyk; Rolf Gericke, both of Seeheim; Inge Lues, Darmstadt; Rolf Bergmann, Reichelsheim; Claus J. Schmitges, Gross-Umstadt, all of Fed. Rep. of Germany

[73] Assignee: Merck Patent Gesellschaft mit beschränkter Haftung, Darmstadt, Fed. Rep. of Germany

[21] Appl. No.: 3,994

[22] Filed: Jan. 16, 1987

[30] Foreign Application Priority Data

Jan. 17, 1986 [DE] Fed. Rep. of Germany ....... 3601196

[51] Int. Cl.$^4$ ............... C07D 211/90; C07D 211/84; C07D 401/06; C07D 491/048
[52] U.S. Cl. ............................. 544/127; 544/131; 544/235; 544/238; 544/277; 544/284; 544/333; 544/353; 544/362; 544/363; 544/364; 544/365; 544/232; 544/243; 544/244; 544/337; 544/405; 546/25; 546/102; 546/113; 546/116; 546/118; 546/122; 546/139; 546/167; 546/194; 546/256; 546/269; 546/270; 546/271; 546/272; 546/273; 546/274; 546/275; 546/278; 546/279; 546/280; 546/281; 546/283; 546/284; 546/286; 546/287; 546/288; 546/289; 546/291; 546/305; 546/315; 546/316; 546/321; 546/322

[58] Field of Search ............... 546/321, 25, 291, 286, 546/305, 287, 315, 288, 316, 289, 322, 102, 269, 113, 270, 116, 271, 118, 272, 122, 273, 194, 274, 139, 275, 167, 278, 256, 279, 280, 281, 283, 284; 544/127, 131, 235, 238, 277, 284, 333, 353, 362, 363, 364, 365, 405, 232, 243, 244, 337

[56] References Cited

U.S. PATENT DOCUMENTS 4,044,141 8/1977 Bossert et al. ............... 546/321

Primary Examiner—M. C. Lee
Assistant Examiner—Dale A. Bjorkman
Attorney, Agent, or Firm—Millen & White

[57] ABSTRACT

Compounds of the formula

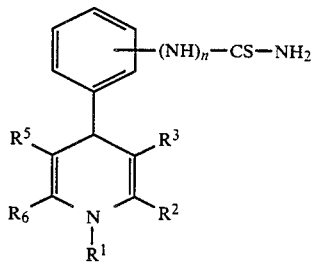

VI are disclosed wherein the variables are herein described. These compounds are intermediates to compounds which influence the influx of calcium into the cell.

2 Claims, No Drawings

1,4-DIHYDROPYRIDINES

The invention relates to new 1,4-dihydropyridines.

SUMMARY OF THE INVENTION

It is an object of the invention to provide new compounds having valuable properties, in particular compounds which can be used for the preparation of medicaments.

Upon further study of the specification and appended claims, further objects and advantages of this invention will become apparent to those skilled in the art.

These objects have been achieved by providing 1,4-dihydropyridines of the formula

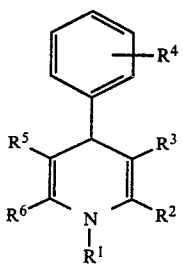

I wherein $R^1$ is H, A, Ar-alkyl, AO-alkyl, ArO-alkyl, Ar-alkyl-O-alkyl or $R^7R^8N$-alkyl, $R^2$ and $R^6$ are each H, A, Ar-alkyl, Hal-alkyl, $CF_3$, $R^9OCH_2—$, $R^7R^8N—(CH_2)_a—CHR^{10}—$, $R^{11}SO_m—CH_2—$, CN or a free or functionally modified CHO group, $R^3$ and $R^5$ are each $R^{12}CO—$, $R^{11}SO_2—$, $(AO)_2PO—$, $NO_2$ or CN, $R^4$ is 4-$R^{13}$-5-$R^{16}$-2-thiazolyl or 4-$R^{13}$-5-$R^{16}$-2-thiazolylamino, $R^7$ is H, A, Ar, AOOC—, Ar—alkyl—OOC—, $R^{10}NHCO—$, $R^{11}SO_2—$ or Ac, $R^8$ is H, A or Ar-alkyl, $R^7$ and $R^8$ together are also Z, $—COCH_2CH_2CO—$, $—COCH=CHCO—$ or $—CO—(o—C_6H_4)—CO—$, $R^9$ is H, A, Ar, Ar-alkyl, AO-alkyl, $R^7R^8N$-alkyl; Ac, $R^{10}NHCO—$, $R^{11}SO_2—$ or $CF_3SO_2—$, $R^{10}$ is H, A or Ar, $R^7$ and $R^{10}$ together are also alkylene having 2–4 C atoms, $R^{11}$ is A or Ar, $R^{12}$ is HO, AO, $R^{14}$—alkyl—O—, $Z=CH—O—$, A, Ar, Het, $R^7R^8N—$ or $R^{15}O$—alkyl—NH—, $R^9$ and $R^{12}$ and $R^8$ and $R^{12}$ together in each case are also a bond, $R^{13}$ and $R^{16}$ are each H, A, AOOC, $AOOCCH_2$, $H_2NCO$, ANHCO, $A_2NCO$, HOOC, Ar-alkyl, Het or a phenyl group which can be monosubstituted to trisubstituted by A, AO, $ASO_m—$, Hal, $CF_3$, HO, $O_2N$, $R^7R^8N$, CN, $H_2NCO$, $H_2NSO_2$, $CHF_2—O—$, $R^7R^8N$-alkyl—O—, Ar or ArO, $R^{14}$ is AO, ArO, Ar—alkyl—O—, $R^7R^8N—$, $R^{15}O_2O—$ or $(AO)_2PO—O—$, $R^{15}$ is H, A, Ar or Ac, a and m are each 0, 1 or 2, A is a linear or branched, saturated or unsaturated, aliphatic or cycloaliphatic hydrocarbon radical having 1–20 C atoms, Ac is $R^{10}CO—$, Ar—alkyl—CO— or Ar—alkenyl-CO—, Ar is phenyl; phenyl which is monosubstituted to trisubstituted by A, AO, AcO, Hal, $CF_3$, HO, $O_2N$, $H_2N$, ANH, $A_2N$, AcNH, AOOCNH—, Ar—alkyl-13 OOCHN—, CN, $H_2NCO$, HOOC, AOOC, $H_2NSO_2$ and/or $R^{11}NHCONH—$; or naphthyl, Hal is F, Cl, Br or I, Het is a 5-membered or 6-membered, mononuclear or polynuclear, heterocyclic radical which has 1–4 O, N and/or S atoms and which can be monosubstituted or polysubstituted by A, AO, Hal, $CF_3$, HO, $O_2N$, $H_2N$, NHA, $NA_2$, AcNH, $ASO_m$, AOOC, CN, $H_2NCO$, HOOC, $H_2NSO_2$, $ASO_2NH$, Ar, Ar-alkenyl and/or pyridyl, or is 1-$R^1$-2-$R^2$-3-$R^3$-5-$R^5$-6-$R^6$-1,4-dihydro-4-pyridyl, and is an alkylene chain which has 4 or 5 C atoms and which can be interrupted by O, HN, AN, ArN, Ar-alkyl-N, $Ar_2CHN$ or AcN, and alkyl or alkenyl are alkylene or alkenylene chains each of which has 1–4 C atoms, and salts thereof.

These objects have also been achieved by providing 1,4-dihydropyridines of the formula

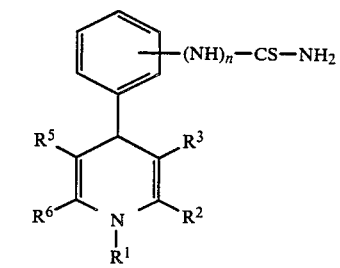

wherein $R^1$, $R^2$, $R^3$, $R^5$ and $R^6$ have the meanings given above and n is 0–1.

DETAILED DISCUSSION

It has been found that the compounds of the formula I have valuable pharmacological properties and are well tolerated. Above all, they influence the influx of calcium into the cell. Thus they display, in particular, effects which are calcium-antagonistic and hence affect the circulation and are vasodilating, hypotensive, anti-arrhythmic and heart-relieving.

The substances reduce the blood pressure measured at the carotid loop of conscious, mongrel dogs (for method cf. E. C. van Leersum, Pflügers Archiv 142, 377–395, 1911) in nephrogenic, hypertonic animals (for method cf. I. H. Page, Science 89, 273–274, 1939) in a test of 10 days duration, when doses which can be less than 2 mg/kg/animal are administered orally, to a lowered level which is dependent on the dosage.

Furthermore, arterial blood pressure measured directly on catheter-carrying (for method cf. J. R. Weeks and J. A. Jones, Proc.Soc.Exptl.Biol.Med. 104, 646–648, 1960), conscious, spontaneously hypertonic rats (strain SHR/NIH/-MO/CHB-EMD), is reduced, after intragastric administration, to an extent dependent on the dosage. The hypotensive effects after intravenous administration can also be verified on narcotized cats by direct measurement of the carotid artery pressure.

The heart-relieving effect can be deduced from the increase in total vascular capacity observed on narcotized dogs after intravenous administration (H. Suga et al., Pflügers Archiv 361, 95–98, 1975).

Some compounds, especially those in which $R^3$ is $NO_2$ or $R^2+R^3$ is $-CH_2-O-CO-$, have a calcium-agonistic, and hence a vasoconstrictive, hypertensive and positive inotropic effect; in addition they can reduce the blood sugar level. This can be demonstrated by means of the glucose DH method (cf. W. Hohenwallner and E. Wimmer, Ärztl.Lab 22, 213–218, 1976)

Furthermore, antithrombotic properties and properties which inhibit platelet aggregation and affect the shape of erythrocytes are found, and also antiallergic, antiasthmatic, microcirculation-promoting, spasmolytic, diuretic, antimetastatic, cytoprotective, antiatherosclerotic, endocrinological (for example affecting the secretion of aldosterone), antidepressant and antiinflammatory effects, which can also be determined by methods which are in use for this purpose.

The compounds of the formula I can, therefore, be used as medicaments in human and veterinary medicine. They can also be used as intermediate products for the preparation of further active compounds for medicaments.

The invention relates to the 1,4-dihydropyridines of the formula I.

For the sake of simplicity, the phenyl radical substituted by $R^4$ will be designated Q in the following text, and the 1-$R^1$-2-$R^2$-5-$R^5$-6-$R^6$-1,4-dihydro-4-pyridyl radical will be designated DHP; the formula I can, accordingly, also be written Q-DHP for short.

In the radicals mentioned, A is preferably an alkyl group which preferably has 1–12, especially 1–8 and specifically preferably 1, 2, 3 or 4, C atoms and is preferably methyl, and is also preferably ethyl, propyl, isopropyl, butyl, isobutyl, sec.-butyl, tert.-butyl, pentyl, isopentyl (3-methylbutyl), hexyl, isohexyl (4-methylpentyl), heptyl, octyl, nonyl, decyl, undecyl or dodecyl, and is also, for example, 1-methylbutyl or 2-methylbutyl, 1,1-, 1,2- or 2,2-dimethylpropyl (neopentyl), 1-ethylpropyl, 1-, 2- or 3-methylpentyl, 1-ethylbutyl or 2-ethylbutyl, 1,1-, 1,2-, 1,3-, 2,2-, 2,3- or 3,3-dimethylbutyl, 1-methyl-1-ethylpropyl, 1-ethyl-2-methylpropyl or 1,1,2-trimethylpropyl or 1,2,2-trimethylpropyl. The group A can, however, also preferably be: alkenyl, in particular alkenyl having 2–8 C atoms, for example vinyl, allyl, 1-propenyl or 1-, 2- or 3-butenyl; alkinyl, in particular alkinyl having 2–8 C atoms, for example ethinyl, propargyl, 1-propinyl or 1-, 2- or 3-butinyl; cycloalkyl, in particular cycloalkyl having 3–9 C atoms, for example cyclopropyl, cyclobutyl, cyclopentyl, cyclohexyl, cycloheptyl, 1-, 2-, 3- or 4-methylcyclohexyl or 1-, 2-, 3- or 4-propylcyclohexyl; cycloalkenyl, in particular cycloalkenyl having 5–7 C atoms, for example 1-cyclopentenyl or 2-cyclopentenyl or 1-, 2- or 3-cyclohexenyl; or cycloalkylalkyl, in particular cycloalkylalkyl having 4–10 C atoms, for example cyclopropylmethyl, 1-cyclopropylethyl or 2-cyclopropylethyl, cyclobutylmethyl, cyclopentylmethyl, 1-cyclopentylethyl or 2-cyclopentylethyl, cyclohexylmethyl, 1-cyclohexylethyl or 2-cyclohexylethyl, 1-, 2- or 3-cyclohexylpropyl or cycloheptylmethyl.

Accordingly, AO is preferably methoxy or ethoxy. AO-alkyl is preferably methoxymethyl, ethoxymethyl, 2-methoxyethyl or 2-ethoxyethyl. $(AO)_2PO-$ is preferably dimethylphosphonyl or diethylphosphonyl. AOOC is preferably methoxycarbonyl or ethoxycarbonyl. AS is preferably methylthio or ethylthio. $A-SO$ is preferably methylsulphinyl or ethylsulphinyl. $A-SO_2$ is preferably methylsulphonyl or ethylsulphonyl. ANH is preferably methylamino or ethylamino. $A_2N$ is preferably dimethylamino or diethylamino. $ASO_2NH$ is preferably methylsulphonamido or ethylsulphonamido and Ac is $H-CO-$, $A-CO-$, $Ar-CO-$, $Ar-alkyl-CO-$, or $Ar-alkenyl-CO-$, preferably formyl, acetyl, propionyl, butyryl, isobutyryl, benzoyl, phenylacetyl or cinnamoyl, and also preferably valeryl, trimethylacetyl, capronyl, tert.-butylacetyl, heptanoyl, octanoyl, o-, m- or p-toluyl, o-, m- or p-methoxybenzoyl, o-, m- or p-acetoxybenzoyl, o-, m- or p-fluorobenzoyl, o-, m- or p-chlorobenzoyl, dichlorobenzoyl, such as 2,4-dichlorobenzoyl, o-, m- or p-bromobenzoyl, o-, m- or p-iodobenzoyl, o-, m- or p-trifluoromethylbenzoyl, o-, m- or p-hydroxybenzoyl, o-, m- or p-nitrobenzoyl, o-, m- or p-tolylacetyl, o-, m- or p-methoxyphenylacetyl, o-, m- or p-acetoxyphenylacetyl, o-, m- or p-fluorophenylacetyl, o-, m- or p-chlorophenylacetyl, dichlorophenylacetyl, such as 2,4-dichlorophenylacetyl, o-, m- or p-methylcinnamoyl, o-, m- or p-methoxycinnamoyl, o-, m- or p-fluorocinnamoyl, o-, m- or p-chlorocinnamoyl or dichlorocinnamoyl, such as 2,4-dichlorocinnamoyl.

Ar is preferably phenyl or monosubstituted phenyl, in particular o-, m- or p-tolyl, o-, m- or p-ethylphenyl, o-, m- or p-propylphenyl, o-, m- or p-isopropylphenyl, o-, m-or p-butylphenyl, o-, m- or p-isobutylphenyl, o- m- or p-hexylphenyl, o-, m- or p-methoxyphenyl, o-, m- or p-ethoxy-phenyl, o-, m- or p-propoxyphenyl, o- m- or p-isopropoxyphenyl, o-, m- or p-butoxyphenyl, o-, m- or p-isobutoxyphenyl, o-, m- or p-hexoxyphenyl, o-, m- or p-fluorophenyl, o-, m- or p-chlorophenyl, o-, m- or p-bromophenyl, o-, m- or p-iodophenyl, o-, m- or p-trifluoromethyl-phenyl, o-, m- or p-hydroxyphenyl, o-, m- or p-nitrophenyl, o-, m- or p-aminophenyl, o-, m- or p-methylaminophenyl, o-, m- or p-ethylaminophenyl, o-, m- or p-dimethylaminophenyl, o-, m- or p-methylethylaminophenyl, o-, m- or p-diethylaminophenyl, o-, m- or p-formamidophenyl, o-, m- or p-acetamidophenyl, o- m- or p-methoxycarbonylaminophenyl, o-, m- or p-ethoxycarbonylaminophenyl, o-, m- or p-cyanophenyl, o-, m- or p-carbamoylphenyl, o-, m- or p-carboxyphenyl, o-, m- or p-methoxycarbonylphenyl, o-, m- or p-ethoxycarbonyl-phenyl, o-, m- or p-aminosulphonylphenyl, o-, m- or p- methylureidophenyl, o-, m- or p-ethylureidophenyl, o-, m- or p-phenylureidophenyl.

Ar can also be a disubstituted phenyl group and also a trisubstituted phenyl group wherein the substituents can be identical or different from one another, for example 2,3-, 2,4-, 2,5-, 2,6-, 3,4- or 3,5-dimethylphenyl, 2,3-, 2,4-, 2,5-, 2,6-, 3,4- or 3,5-dimethoxyphenyl, 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dihydroxyphenyl, 3,4-diaminophenyl, 3-methoxy-4-hydroxyphenyl, 3-hydroxy-4-methoxyphenyl, 3-nitro-4-hydroxyphenyl, 3-amino-4-hydroxyphenyl or 3,4,5-trimethoxyphenyl. Ar can also be 1-naphthyl or 2-naphthyl.

Phenyl is a particularly preferred Ar radical. Accordingly, Ar-alkyl is preferably benzyl, 1-phenylethyl or 2-phenylethyl, ArO-alkyl is preferably phenoxymethyl, 1-phenoxyethyl or 2-phenoxyethyl, and Ar-alkyl-O-alkyl is preferably benzyloxymethyl, 2-benzyloxyethyl, 2phenylethoxymethyl or 2-(2-phenylethoxy)-ethyl. Ar-alkyl-OOC- is preferably benzyloxycarbonyl or 2-phenylethoxycarbonyl. Ar-alkenyl is preferably styryl (=2-phenylvinyl) and also styrylmethyl (=3-phenyl-2-propen-1-yl). Ar-alkyl-O is preferably benzyloxy, 1-phenylethoxy or 2-phenylethoxy.

Het is preferably 2-furyl or 3-furyl, 2-thienyl or 3-thienyl, 1-, 2- or 3-pyrryl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidyl, and also, preferably, 1,2,3-triazol-1-, -4- or -5-yl, 1,2,4-triazol-1-, -3- or -5-yl, 1-tetrazolyl or 5-tetrazolyl, 1,2,3-oxadiazol-4-yl or 1,2,3-oxadiazol-5-yl, 1,2,4-oxadiazol-3-yl or 1,2,4-oxadiazol-5-yl, 1,3,4- thiadiazol-2-yl or 1,3,4-thiadiazol-5-yl, 1,2,4-thiadiazol-3-yl or 1,2,4-thiadiazol-5-yl, 2,1,5-thiadiazol-3-yl or 2,1,5-thiadiazol-4-yl, 2-, 3-, 4-, 5- or 6-2H-thiopyranyl, 2-, 3- or 4-4H-thiopyranyl, 3-pyridazinyl or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-indolyl, 1-, 2-, 3-, 4-, 5-, 6- or 7-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6-or 7-benzoisoxazolyl, 2-, 4-, 5-, 6- or 7-benzothiazolyl, 2-, 4-, 5-, 6- or 7-benzoisothiazolyl, 4-, 5-, 6- or 7-benzo-2,1,3-oxadiazolyl, 2-, 3-, 4-, 5-, 6-, 7-, or 8quinolyl, 1-, 3-, 4-, 5-, 6-, 7- or 8-isoquinolyl, 1-, 2-, 3-, 4- or 9-carbazolyl, 1-, 2-, 3-, 4-, 5-, 6-, 7-, 8- or 9-acridinyl, 3-, 4-, 5-, 6-, 7- or 8-cinnolyl, 2-, 4-, 5-, 6-, 7- or 8-quinazolyl, 2-, 3-, 5', 6-, 7- or 8-quinoxalyl, 1-, 2-, 5-, 6- or 7-1H-imidazo[4,5-b]pyridyl, 1-, 2-, 4-, 6- or 7-1H-imidazo[4,5-c]pyridyl, 2-, 6-, 8- or 9-puryl. The heterocyclic radicals can also be partly or completely hydrogenated. Het can, therefore, also be, for example: 2,3-dihydro-2-, -3-, -4- or -5-furyl, 2,5-dihydro-2-, -3-, -4- or -5-furyl, tetrahydro-2-furyl or tetrahydro-3-furyl, tetrahydro-2-thienyl or tetrahydro-3-thienyl, 2,3-dihydro-1-, -2-, -3-, -4- or -5-pyrryl, 2,5-dihydro-1-,-2-,-3-,-4- or -5-pyrryl, 1-, 2- or 3-pyrrolidinyl, tetrahydro-1-, -2- or -4-imidazolyl, 2,3-dihydro-1-, -2-, -3-, -4- or 5-pyrazolyl, 2, -2-, -3-, -4- or 5-pyrazolyl, tetrahydro-1-, -3-, or -4pyrazolyl, 1,4-dihydro-1-, -2-, -3- or -4-pyridyl, 1,2,3, 4-tetrahydro-1-, -2-, -3-, -4-, -5- or -6-pyridyl, 1,2,3, 6-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidyl, 1-, 2- or 3-piperazinyl, 1,2,3, 4-tetrahydro-1-, -2-, -3-, -4-, -5-, -6-, -7- or -8-quinolyl, 1,2,3,4- tetrahydro-1-, -2-, -3-, -4-, -5-, -6-, -7- or 8-isoquinolyl. Het can have typically 1 or 2 nuclei, 1 or 2 substituents and can be heteroaliphatic or heteroaromatic. Typically, as mentioned, each ring has 5 or6 atoms in it.

The heterocyclic radicals can also be substituted as indicated. Het can, therefore, also be, for example: 3-, 4- or 5-methyl-2-furyl, 2-, 4- or 5-methyl-3-furyl, 2,4-dimethyl-3-furyl, 5-nitro-2-furyl, 5-styryl-2-furyl, 3-, 4- or 5-methyl-2-thienyl, 2-, 4- or 5-methyl-3-thienyl, 3-methyl-5-tert.-butyl-2-thienyl, 5-chloro-2-thienyl, 5-phenyl-2-thienyl or 5-phenyl-3-thienyl, 1-, 3-, 4- or 5-methyl-2-pyrryl, 1-methyl-4-nitro-2-pyrryl or 1-methyl-5-nitro-2-pyrryl, 3,5-dimethyl-4-ethyl-2-pyrryl, 4-methyl-5-pyrazolyl, 4-methyl-2-thiazolyl or 5-methyl-2-thiazolyl, 2-methyl-4-thiazolyl or 5-methyl-4-thiazolyl, 2-methyl-5-thiazolyl or 4-methyl-5-thiazolyl, 2,4-dimethyl-5-thiazolyl, 3-, 4-, 5- or 6-methyl-2-pyridyl, 2-, 4-, 5- or 6-methyl-3-pyridyl, 2-methyl-4-pyridyl or 3-methyl-4pyridyl, 3-, 4-, 5- or 6-chloro-2-pyridyl, 2-, 4-, 5- or 6-chloro-3-pyridyl, 2-chloro-4-pyridyl or 3-chloro-4pyridyl, 2,6-dichloropyridyl, 5-methyl-4-pryimidyl or 6-methyl-4-pyrimidyl, 2,6-dihydroxy-4-pyrimidyl, 5-chloro-2-methyl-4-pyrimidyl, 3-methyl-2-benzofuryl, 2-ethyl-3benzofuryl, 7-methyl-2-benzothienyl, 1-, 2-, 4-, 5-, 6or 7-methyl-3-indolyl, 1-methyl-5-benzimidazolyl or 1-methyl-6-benzimidazolyl, 1-ethyl-5-benzimidazolyl or 1-ethyl6-benzimidazolyl, or 3-, 4-, 5-, 6-, 7 or 8-hydroxy-2-quinolyl.

Z is preferably tetramethylene, pentamethylene, 3-oxapentamethylene, 3-azapentamethylene or 3-A-azapentamethylene, such as 3-methylazapentamethylene, 3-Ac-azapentamethylene, such as 3-acetylazapentamethylene, 3-Arazapentamethylene, such as 3-phenylazapentamethylene, 3-Ar-alkylazapentamethylene, such as 3-benzylazapentamethylene, or 3-Ar$_2$CH-azapentamethylene, such as 3-diphenylmethylazapentamethylene. Typically the alkylene chain Z is interrupted by 0 or 1 of said groups.

Specifically, $R^1$ is preferably H and, as a second preference, is methyl, ethyl, benzyl, 2-methoxyethyl, 2-phenoxyethyl, 2-benzyloxyethyl, 2-dimethylaminoethyl, 2-diethylaminoethyl, 2-pyrrolidinoethyl, 2-piperidinoethyl or 2-morpholinoethyl.

$R^2$ and $R^6$ are identical or different and are each preferably A, in particular alkyl having 1–8C atoms or cycloalkyl having 3–7C atoms, preferably methyl and also preferably H, phenyl, benzyl, chloromethyl, bromomethyl, hydroxymethyl or 2-aminoethoxymethyl; it is particularly preferable for $R^2$ and $R^6$ to be identical and to be methyl.

$R^3$ and $R^5$ are identical or different and are each preferably $R^{12}CO—$, in particular AOOC (wherein A is preferably alkyl having 1–8C atoms, preferably methyl, ethyl or isopropyl, or cycloalkyl having 3–7C atoms), and also 2-alkoxyethoxycarbonyl (wherein alkoxy preferably has 1–4C atoms), in particular 2-methoxyethoxycarbonyl, 2-ethoxyethoxycarbonyl or 2-propoxyethoxycarbonyl, 2-N,N-dialkylaminoethoxycarbonyl (wherein the alkyl groups each preferably contain 1–4C atoms) or 2-N-alkyl-N-aralkylaminoethoxycarbonyl (wherein the alkyl group preferably contains 1–4C atoms and the aralkyl group preferably contains 7–10C atoms), such as 2-N-methyl-N-benzylaminoethoxycarbonyl It is also possible for one of the groups $R^3$ or $R^5$ preferably to be $NO_2$ or CN.

The groups $R^2$ and $R^3$ together can also preferably be $—CH_2—O—CO—$ and can thus, together with the 1,4-dihydropyridine ring, form a 5-oxo-1,4,5,7-tetrahydrofuro[3,4-b]pyridine.

$R^4$ is preferably in the o-position, and also preferably in the m-position, of the phenyl ring and is preferably 4-$R^{13}$-5-$R^{16}$-2-thiazolylamino.

$R^7$ is preferably H, A (in particular alkyl having 1–4 C atoms), Ar (in particular phenyl or methoxyphenyl) or Ac (in particular alkanoyl having 1–4C atoms, benzoyl or phenylacetyl).

$R^8$ is preferably H, A (in particular alkyl having 1–4C atoms) or benzyl.

Accordingly, the group $R^7R^8N$ is preferably amino, methyl-, ethyl-, propyl-, butyl-, benzyl-, dimethyl-, diethyl-, dipropyl-, dibutyl-, N-methyl-N-benzylamino, N-methyl-N-p-methoxybenzylamino, formamido, acetamido, propionamido, benzamido, N-methylformamido or N-methyl-acetamido.

Together with the N atom to which they are attached, $R^7$ and $R^8$ are also preferably pyrrolidino, piperidino, morpholino, piperazino, N-methylpiperazino, N-acetylpiperazino, N-phenylpiperazino, N-benzylpiperazino, N-diphenylmethylpiperazino, succinimido, maleinimido or phthalimido $R^9$ is preferably H, and also preferably Ac (in particular alkanoyl having 1–4C atoms).

$R^{10}$ is preferably H, A (in particular alkyl having 1–4C atoms) or phenyl $R^{11}$ is preferably A (in particular alkyl having 1–4C atoms) or phenyl.

$R^{12}$ is preferably AO (in particular alkoxy having 1–4C atoms), and also preferably AO-alkoxy (in particular alkoxyethoxy having 3–6C atoms) or alkoxy (in particular dialkylaminoalkoxy having 4–10C atoms or N-alkyl-N-Ar-alkylaminoalkoxy having 10–18C atoms).

$R^{13}$ and $R^{16}$ are preferably phenyl; monosubstituted phenyl wherein the substituent is preferably in the p-position, preferably alkylphenyl, such as o-, m- or p-tolyl, o-, m- or p-ethylphenyl, or o-, m- or p-tert.butylphenyl; alkoxyphenyl, such as o-, m- or p-methoxyphenyl, or o-, m- or p-ethoxyphenyl; alkylthiophenyl, such as o-, m- or p-methylthiophenyl; alkylsulphinylphenyl, such as o-, m- or p-methylsulphinylphenyl; alkylsulphonylphenyl, such as o-, m- or p-methylsulphonylphenyl; halogenophenyl, such as o-, m- or p-fluorophenyl, o-, m- or p-chlorophenyl, o-, m- or p-bromophenyl, o-, m- or p-iodophenyl; o-, m- or p-trifluoromethylphenyl; o-, m- or p- hydroxyphenyl; o-, m- or p-nitrophenyl; o-, m- or p-aminophenyl; alkylaminophenyl, such as o-, m- or p-methylaminophenyl; dialkylaminophenyl, such as o-, m- or p-dimethylaminophenyl or o-, m- or p-diethylaminophenyl; o-, m- or p-pyrrolidinophenyl; o-, m- or p-piperidinophenyl; o-, m- or p-morpholinophenyl; o-, m- or p-piperazinophenyl; 4-alkylpiperazinophenyl, such as o-, m- or p-4-methylpiperazinophenyl; 4-acylpiperazinophenyl, such as o-, m- or p-4-acetylpiperazinophenyl; 4-arylpiperazinophenyl, such as o-, m- or p-4-phenylpiperazinophenyl, o-, m- or p-4-(o-methoxyphenyl)-piperazinophenyl; o-, m- or p-4-(p-methoxyphenyl)-piperazinophenyl; 4-Ar-alkylpiperazinophenyl, such as o-, m- or p-4-benzylpiperazinophenyl; 4diarylmethylpiperazinophenyl, such as o-, m- or p-4-diphenylmethylpiperazinophenyl; alkanoylaminophenyl, such as o-, m- or p-acetamidophenyl; aroylaminophenyl, such as o-, m- or p-benzamidophenyl, o-, m- or p-(o-, m- or p- toluylamido)-phenyl, o-, m- or p-(o-, m- or p-methoxybenzamido)-phenyl, o-, m- or p-(o-, m- or p-chlorobenzamido)-phenyl, or o-, m- or p-(2,4-dichlorobenzamido)phenyl; alkoxycarbonylaminophenyl, such as o-, m- or p-ethoxycarbonylaminophenyl; o-, m- or p-phthalimidophenyl; o-, m- or p-isoindolinophenyl; o-, m- or p-ureidophenyl; N'-alkylureidophenyl, such as o-, m- or p-N'-methylureidophenyl; N'-arylureidophenyl, such as o-, m- or p-N'-phenylureidophenyl; o-, m- or p-cyanophenyl; o-, m- or p-carbamoylphenyl, o-, m- or p-aminosulphonylphenyl; o-, m- or p-difluoromethoxyphenyl; o-, m- or p-2,2-difluoroethoxyphenyl; o-, m- or p-dialkylaminoalkoxyphenyl, such as o-, m- or p-2-dimethylaminoethoxyphenyl, or o-, m- or p-2- diethylaminoethoxyphenyl; Ar-phenyl, such as 2-, 3- or 4-biphenylyl; aryloxyphenyl, such as o-, m- or p-phenoxyphenyl; disubstituted phenyl, preferably 2,3-, 2,4-, 2,5-, 2,6-, 3,4- or 3,5-dimethylphenyl, -dimethoxyphenyl, -difluorophenyl, -dichlorophenyl or -dihydroxyphenyl, 3-methoxy-4-hydroxyphenyl, 3-hydroxy-4-methoxyphenyl, 3-nitro-4-methoxyphenyl or 3-acetamido-4-trisubstituted phenyl, preferably 2,3,4-, 2,3,5-, 2,3,6-, 2,4,5-, 2,4,6- or 3,4,5-trimethylphenyl -trimethoxyphenyl or -trifluorophenyl, 2,6-dimethyl-4-tert.-butylphenyl or 2,4-dimethoxy-5-bromophenyl; Het, such as, preferably, 2-furyl or 3-furyl, 2-thienyl or 3-thienyl, 1-, 2- or 3pyrryl, 1-methyl-2-pyrryl, 2-, 3- or 4-pyridyl, 3-cyano-6-methyl-2-oxo-1,2-dihydro-5-pyridyl or one of the other radicals mentioned above as preferred for Het; and also hydrogen; alkyl having preferably 1–4C atoms, such as methyl, ethyl, propyl, isopropyl, butyl, isobutyl, sec.-butyl or tert.-butyl; alkoxycarbonyl, such as methoxycarbonyl or ethoxycarbonyl; alkoxycarbonylmethyl, such as methoxycarbonylmethyl or ethoxycarbonylmethyl; carbamoyl; N-alkylcarbamoyl, such as N-methylcarbamoyl or N-ethylcarbamoyl; N,N-dialkylcarbamoyl, such as N,N-dimethylcarbamoyl or N,N-diethylcarbamoyl; carboxyl; or Aralkyl, such as benzyl, 1-phenylethyl or 2-phenylethyl.

Particularly preferably $R^{13}$ is phenyl, o-, m- or p-tolyl, o-, m- or p-methoxyphenyl, o-, m- or p-fluorophenyl, o-, m- or p-chlorophenyl, o-, m- or p-trifluoromethylphenyl or 3,4-dichlorophenyl, and $R^{16}$ is preferably H and also methyl, phenyl or benzyl.

$R^{14}$ is preferably AO having 1–4C atoms, such as methoxy, ethoxy, propoxy or butoxy, and also preferably $R^{15}$ is preferably H or A, in particular alkyl having 1–4C atoms.

The parameters a and m are preferably 0 or 1.

Accordingly, the invention relates in particular to compounds of the formula I in which at least one of the said radicals or parameters has one of the preferred meanings indicated above.

Some preferred groups of compounds can be expressed by the following partial formulae Ia to Ii, which correspond to the formula I and wherein the radicals not described in detail have the meanings indicated in formula I, but wherein in Ia $R^4$ is 4-$R^{13}$-5-$R^{16}$-2-thiazolyl;

in Ib $R^4$ is 4-$R^{13}$-5-$R^{16}$-2-thiazolyl, $R^{13}$ is a phenyl group which can be monosubstituted to trisubstituted by A, AO, ASO$_m$-, Hal, CF$_3$, HO, O$_2$N, R$^7$R$^8$N, CN, H$_2$NCO, H$_2$NSO$_2$, CHF$_2$—O—, R$^7$ and R$^8$N—alkyl—O—, Ar or ArO, and $R^{16}$ is H;

in Ic $R^4$ is 4-$R^{13}$-5-$R^{16}$-2-thiazolyl, $R^{13}$ is phenyl, tolyl, methoxyphenyl, chlorophenyl or dichlorophenyl, and $R^{16}$ is H;

in Id $R^4$ is 4-$R^{13}$-5-$R^{16}$-2-thiazolylamino;

in Ie $R^4$ is 4-$R^{13}$-2-thiazolylamino;

in If $R^4$ is 4-$R^{13}$-5-$R^{16}$-2-thiazolylamino, $R^{13}$ is H, A, AOOC, AOOCCH$_2$, Het or a phenyl group which can be monosubstituted to trisubstituted by A, AO, ASO$_m$-, Hal, CF$_3$, HO, O$_2$N, CN, H$_2$NCO, H$_2$NSO$_2$, CHF$_2$—O—, R$^7$R$^8$N—alkyl—O—, Ar or ArO, and $R^{16}$ is H, A, benzyl or a phenyl group which can be monosubstituted to trisubstituted by A, AO, ASO$_m$-, Hal, CF$_3$, HO, O$_2$N, R$^7$R$^8$N, CN, H$_2$NCO, H$_2$NSO$_2$, CHF$_2$—O—, R$^7$R$^8$N-alkyl—O—Ar or ArO;

in Ig $R^4$ is 4-$R^{13}$-5-$R^{16}$-2-thiazolylamino, $R^{13}$ is H, A, AOOC, AOOCCH$_2$, pyridyl, 3-cyano-6-methyl-2-pyridon-5-yl or a phenyl group which can be monosubstituted to trisubstituted by A, AO, Hal, CF$_3$, HO, O$_2$N, A—CO—NH, CN, H$_2$NSO$_2$ or phenyl, and $R^{16}$ is H, A, benzyl or phenyl;

in Ih $R^4$ is 4-$R^{13}$-5-$R^{16}$-2-thiazolylamino, $R^{13}$ is a phenyl group which can be monosubstituted by $CH_3$, $CH_3O$, F, Cl or $CF_3$ or disubstituted by Cl, and
$R^{16}$ is H; and
in Ii $R^4$ is 4-$R^{13}$-5-$R^{16}$-2-thiazolylamino,
$R^{13}$ is phenyl, p-tolyl, p-methoxyphenyl, p-fluorophenyl, m-chlorophenyl, p-chlorophenyl, m-trifluoromethylphenyl or 3,4-dichlorophenyl, and
$R^{16}$ is H.

Compounds which are also preferred are those of the partial formulae I' and Ia' to Ii' which correspond to the formulae I and Ia to Ii and wherein, in addition, $R^2$ and $R^6$ are each methyl groups.

Compounds which are also preferred are those of the partial formulae I'' and Ia'' to Ii'' which correspond to the formulae I and Ia to Ii and in each of which, additionally, $R^3$ and $R^5$ are each AOOC and the two radicals A (identical or different) are alkyl groups having 1–4 C atoms.

Compounds which are particularly preferred are those of the partial formulae I''' and Ia''' to Ii''' which correspond to the formulae I and Ia to Ii and in each of which, in addition,
$R^2$ and $R^6$ are each $CH_3$,
$R^3$ and $R^5$ are each AOOC and
A is an alkyl group having 1–4 C atoms, it being possible, if several groups A are present in the molecule, for these to be identical or different from one another.

Amongst the compounds of the formulae I, I', I'', I''', Ia to Ii, Ia' to Ii', Ia'' to Ii'' and Ia''' to I''', preferred compounds are in each case those in which the radical $R^1$ is H and/or in which the radical $R^4$ is in the o-position or m-position, especially in the o-position.

The invention also relates to a process for the preparation of dihydropyridines of the formula I and their salts, characterized in that compounds of the formulae II, III, IV and V $R^1$—$NH_2$     II
$R^2$—CO—$CH_2$—$R^3$     III
$R^6$—CO—$CH_2$—$R^5$     IV

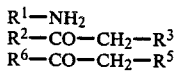

V

CHO or functional derivatives thereof are reacted with one another, if desired in stages, or a thioamide of the formula VI

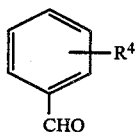

VI wherein
n is 0 or 1 is reacted with a carbonyl compound of the formula VII $R^{16}$—CHX—CO—$R^{13}$     VII wherein X is Cl, Br, I or a free or reactive, esterified OH group, or a compound of the formula VIII

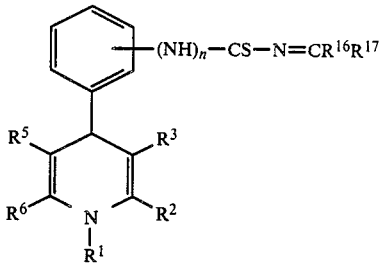

VIII wherein $R^{17}$ is HO, AO or $A_2N$ is reacted with a compound of the formula IX $R^{13}$—$CH_2$—X     IX and/or, in a compound of the formula I, one or more of the radicals $R^1$, $R^2$, $R^3$, $R^4$, $R^5$, and/or $R^6$ are converted into other radicals $R^1$, $R^2$, $R^3$, $R^4$, $R^5$ and/or $R^6$, and/or a basic or acid compound of the formula I is converted into one of its salts by treatment with an acid or base, respectively.

The preparation of the compounds of the formula I is effected in other respects by processes which are in themselves known, such as are described in the literature (for example in standard works such as Houben-Weyl, Methoden der Organischen Chemie, ("Methods of Organic Chemistry"), Georg-Thieme-Verlag, Stuttgart), specifically under reaction conditions such as are known and are suitable for the reactions mentioned. In this regard it is also possible to make use of variants which are in themselves known but are not mentioned here in detail.

Those skilled in the art can select appropriate methods of synthesis from the state of the art by routine methods.

The starting materials can, if desired, also be formed in situ in a procedure in which they are not isolated from the reaction mixture, but are immediately reacted further to give the compounds of the formula I.

On the other hand, it is possible to carry out the reaction in stages. Thus it is possible first to react some of the starting materials II, III, IV and V with one another, and then to react the intermediate products obtained with the remaining starting materials.

Thus it is possible to obtain compounds of the formula I not only by means of the reaction (a):

(a) II+III+IV+V but also, for example, by means of the reactions (b) to (d):

(b) $R^2$—CO—$CR^3$=CH—Q (=X; obtainable from III+V)+II+IV or
$R^6$—CO—$CR^5$=CH—Q (=XI; obtainable from IV+V)+II+III;

(c) X+$R^1$NH—$CR^6$=$CHR^5$ (=XII; obtainable from II+IV) or XI+$R^1$NH—$CR^2$=$CHR^3$ (=XIII; obtainable from II+III); or (d) $R^2$—CO—$CHR^3$—CHQ—$CHR^5$—CO—$R^6$ (=XIV; obtainable from III+IV +V)+II.

Instead of the starting materials mentioned, it is also possible to employ functional derivatives of these compounds in the reaction. Examples of suitable derivatives of this type are enamines (such as XII and XIII), enol ethers, for example trialkylsilyl enol ethers, such as trimethylsilyl or dimethyltert.-butylsilyl enol ethers, methyl esters of tetronic acid or enol esters, for example enol acetate, enol methanesulphonates or enol p-toluene sulphonates of III and IV, acetals or hemi-acetals of V, or salts (for example hydrochlorides, sulphates, nitrates or acetates) of II. The starting materials of the formulae II to V and X to XIV are known from the literature or can be prepared by methods known from the literature (cf. for example Houben-Weyl, loc. cit.).

Examples of typical starting materials of the formula II are ammonia, which can be used in the gaseous state or in aqueous or non-aqueous solution, and also alkylamines, such as methylamine or ethylamine, aralkylamines, such as 2-methoxyethylamine or 2-ethoxyethylamine, aryloxyalkylamines, such as 2-phenolethylamine, aralkoxyalkylamines, such as 2-benzyloxyethylamine, aminoalkylamines, such as 2-dimethylaminoethylamine, 2-diethylaminoethylamine, 2-pyrrolidinoethylamine, 2-piperidinoethylamine, 2-morpholinoethylamine, 2-piperazinoethylamine, 2-(4-methylpiperazino)-ethylamine or 2-(4-phenylpiperazino)-ethylamine or 3-dimethylaminopropylamine, 3-diethylaminopropylamine, 3-pyrrolidinopropylamine, 3-piperidinopropylamine, 3-morpholinopropylamine, 3-piperazinopropylamine, 3-(4-methylpiperazino)-propylamine or 3-(4-phenylpiperazino)-propylamine.

Typical starting materials ot the formulae III and IV are acetoacetic acid methyl, ethyl, isopropyl, isobutyl, 2-methoxyethyl, 2-propoxyethyl, 2-phenoxyethyl, 2-benzyloxyethyl, 2-dimethylaminoethyl or 2-(N-benzyl-N-methylamino)-ethyl ester, and also malonaldehydic acid methyl, ethyl or isopropyl ester, 3-oxo-4-phenylbutyric acid methyl, ethyl or isopropyl ester, 3-oxo-4-chlorobutyric acid methyl, ethyl or isopropyl ester, 3-oxo-4-bromobutyric acid methyl, ethyl or isopropyl ester, 3-oxo-4,4,4-trifluorobutyric acid methyl, ethyl or isopropyl ester, 3-oxo-4-hydroxybutyric acid methyl, ethyl, or isopropyl ester, 3-oxo-4-acetoxybutyric acid methyl, ethyl or isopropyl ester, 3-oxo-4-carbamoyloxybutyric acid methyl, ethyl or isopropyl ester, 3-oxo-4-dimethylaminobutyric acid methyl, ethyl or isopropyl ester, 3-oxo-4-methylthiobutyric acid methyl, ethyl or isopropyl ester, 3-oxo-4-methylthiobutyric acid methyl, ethyl or isopropyl ester, 3-oxo-4-methylsulphinylbutyric acid methyl, ethyl or isopropyl ester, 3-oxo-4-methylsulphonylbutyric acid methyl, ethyl or isopropyl ester, 3-oxo-3-cyanopropionic acid methyl, ethyl or isopropyl ester, 2-oxosuccinic acid dinitrile, 3,4-dioxobutyric acid methyl, ethyl or isopropyl ester, acetylacetone, hexane-2,5-dione, heptane-2,5-dione, benzoylacetone, 2-acetoacetylthiophene, acetoacetamide, acetoacetic acid N-methylamide, N,N-dimethylamide, pyrrolidide, piperidide, morpholide, 2-hydroxyethylamide, 2-methoxyethylamide, 2-phenoxyethylamide or 2-acetoxyethylamide, methylsulphonylacetone, phenylsulphonylacetone, dimethylphosphonylacetone, diethylphosphonylacetone, nitroacetone, cyanoacetone or tetronic acid.

Typical starting materials of the formula V are those of formulae Va and Vb wherein the substituents are preferably in the o-position, and also preferably in the m-position, relative to the aldehyde group:

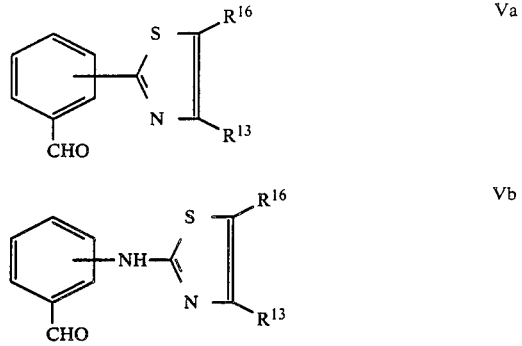

Amongst these, those of the formula Va are preferred, for example 2-(o-formylphenyl)-4-phenylthiazole,
2-(m-formylphenyl)-4-phenylthiazole,
2-(o-formylphenyl)-4-o-, -m- or -p-tolylthiazole,
2-(m-formylphenyl)-4-o-, -m- or -p-tolylthiazole,
2-(o-formylphenyl)-4-o-, -m- or -p-methoxyphenylthiazole,
2-(m-formylphenyl)-4-o-, -m- or -p-methoxyphenylthiazole,
2-(o-formylphenyl)-4-o-, -m- or -p-fluorophenylthiazole,
2-(m-formylphenyl)-4-o-, -m- or -p-fluorophenylthiazole,
2-(o-formylphenyl)-4-o-, -m- or -p-chlorophenylthiazole
2-(m-formylphenyl)-4-o-, -m- or -p-chlorophenylthiazole,
2-(o-formylphenyl)-4-o-, -m- or -p-trifluoromethylphenylthiazole, or
2-(m-formylphenyl)-4-o-, -m- or -p-trifluoromethylphenylthiazole.

The following are examples of compounds of the formula Vb which are preferred:
2-(o-formylanilino)-4-phenylthiazole,
2-(m-formylanilino)-4-phenylthiazole,
2-(o-formylanilino)-4-o-, -m- or -p-tolylthiazole,
2-(m-formylanilino)-4-o-, -m- or -p-tolylthiazole,
2-(o-formylanilino)-4-o-, -m- or -p-methoxyphenylthiazole,
2-(m-formylanilino)-4-o-, -m- or -p-methoxyphenylthiazole,
2-(o-formylanilino)-4-o-, -m- or -p-fluorophenylthiazole,
2-(m-formylanilino)-4-o-, -m- or -p-fluorophenylthiazole,
2-(o-formylanilino)-4-o-, -m- or -p-chlorophenylthiazole,
2-(m-formylanilino)-4-o-, -m- or -p-chlorophenylthiazole,
2-(o-formylanilino)-4-o-, -m- or -p-trifluoromethylphenylthiazole, or
2-(m-formylanilino)-4-o-, -m- or -p-trifluoromethylphenylthiazole.

The following are examples of typical starting compounds of the formulae X and XI: 2-acetyl-o-(4-phenyl-2-thiazolyl)-cinnamic acid methyl, ethyl or isopropyl ester or 2-acetyl-m-(4-phenyl-2-thiazolyl)-cinnamic acid methyl, ethyl or isopropyl ester and also the corresponding 4-o-, -m- or -p-tolyl-2-thiazolyl, 4-o-, -m- or -p-methoxyphenyl-2-thiazolyl, 4-o-, -m- or -p-fluorophenyl-2-thiazolyl, 4-o-, -m- or -p-chlorophenyl- 2-thiazolyl or 4-o-, -m- or -p-trifluoromethylphenyl-2-thiazolyl derivatives.

Examples of typical starting materials of the formulae XII and XIII are those of the formula $H_2N-C(CH_3)=C-CO-R^{12}$, such as 3-aminocrotonic acid methyl, ethyl, isopropyl, isobutyl, 2-methoxyethyl, 2-propoxyethyl, 2-phenoxyethyl, 2-benzyloxyethyl, 2-dimethylaminoethyl or 2-(N-benzyl-N-methylamino)-ethyl ester, 3-methylaminocrotonic acid methyl, ethyl or isopropyl ester, 3-(2-morpholinoethylamino)-crotonic acid methyl, ethyl or isopropyl ester and tetronamide.

Examples of typical starting materials of the formula XIV are 3,5-diethoxycarbonyl-4-o-(4-phenyl-2-thiazolyl)-phenyl-2,6-heptanedione or 3,5-diethoxycarbonyl-4-m-(4-phenyl-2-thiazolyl)-phenyl-2,6-heptanedione and corresponding 4-o-, -m- or -p-tolylphenyl-2-thiazolyl, 4-o-, -m- or -p-methoxyphenyl-2-thiazolyl, 4-o-, -m- or -p-fluorophenyl-2-thiazolyl, 4-o-, -m- or -p-chlorophenyl-2-thiazolyl or 4-o-, -m- or -p-trifluoromethylphenyl-2-thiazolyl derivatives.

The reactions (a), (b), (c) and (d) defined above are carried out, as a rule, under the conditions of the Hantzsch Synthesis of 1,4-dihydropyridines (cf, for example, The Merck Index, Tenth Edition, Merck & Co., Inc., Rahway, N.J., U.S.A., 1983, page ONR-39 and the literature quoted therein). The starting materials of the formulae III to V and also X to XIV are, as a rule, employed in stoichiometric amounts or in a slight excess or less than stoichiometric amount, while those of the formula II —particularly if $R^1=H$—are employed in a slight or fairly large excess.

These reactions are carried out in the absence or—preferably—in the presence of an inert solvent or diluent. Examples of suitable solvents are alcohols, such as methanol, ethanol, propanol or isopropanol; ethers, such as diethyl or diisopropyl ether, tetrahydrofuran, dioxane or ethylene glycol monomethyl or dimethyl ether; carboxylic acids, such as acetic acid; nitriles, such as acetonitrile; esters, such as ethyl acetate; amides, such as dimethylformamide (DMF), dimethylacetamide or phosphoric acid hexamethyltriamide; sulphoxides, such as dimethyl sulphoxide; hydrocarbons, such as hexane, cyclohexane, benzene or toluene; chlorinated hydrocarbons, such as methylenedichloride, chloroform, carbontetrachloride, trichloroethylene or 1,2-dichloroethane; or amines, such as pyridine. Mixtures of these solvents with one another and mixtures with water are also suitable. In general, the reactions are carried out at reaction temperatures between 20° and 150°, preferably 50° and 100°, but especially at the boiling point of the particular solvent.

In general the reaction is carried out under normal pressure; it can, however, also be carried out under an elevated pressure of up to about 100 bar, particularly if low-boiling solvents are used.

The compounds of the formula I are also obtainable by reacting compounds of the formula VI with compounds of the formula VII. In particular, compounds of the formula Id can be prepared from thioureas of the formula VI (n=1). These, in turn, are accessible from the corresponding nitro compounds of the formula $DHP-C_6H_4-NO_2$ by reduction to give the amines of the formula $DHP-C_6-H_4-NH_2$, reaction with benzoyl isothiocyanate (preferably prepared in situ from NaSCN and benzoyl chloride in acetone) to give the benzoylthioureas of the formula $DHP-C_6-H_4-N-H-CS-NH-COC_6H_5$ and splitting off the benzoyl group with $K_2CO_3$ in aqueous methanol. The thioamides of the formula VI (n=0) can be obtained, for example, from the nitriles of the formula $DHP-C_6-H_4-CN$ by means of $H_2S$.

Typical starting materials of the formula VI are 2,6-dimethyl-3,5-dimethoxycarbonyl-4-o-thioureidophenyl-1,4-dihydropyridine, 2,6-dimethyl-3,5-dimethoxycarbonyl-4-m-thioureidophenyl-1,4-dihydropyridine, 2,6-dimethyl-3,5-diethoxycarbonyl-4-o-thioureidophenyl-1,4-dihydropyridine, 2,6-dimethyl-3,5-diethoxycarbonyl-4-m-thioureidophenyl-1,4-dihydropyridine 2,6-dimethyl-3,5-dimethoxycarbonyl-4-o-aminothiocarbonylphenyl-1,4-dihydropyridine, 2,6-dimethyl-3,5-dimethoxycarbonyl-4-m-aminothiocarbonylphenyl-1,4-dihydropyridine and 2,6-dimethyl-3,5-diethoxycarbonyl-4-o-aminothiocarbonylphenyl-1,4-dihydropyridine and 2,6-dimethyl-3,5-diethoxycarbonyl-4-m-aminothiocarbonylphenyl-1,4-dihydropyridine.

In the compounds of the formula VII—most of which are known—X is preferably Cl or Br, but also a reactive, esterified OH group such as alkylsulphonyloxy having, in particular, 1–4 C atoms (for example methanesulphonyloxy) or arylsulphonyloxy having, in particular, 6–10 C atoms (for example benzenesulphonyloxy, p-toluenesulphonyloxy, 1-naphthalenesulphonyloxy or 2-naphthalenesulphonyloxy).

Typical compounds of the formula VII are α-chloroacetophenone, α-bromoacetophenone, α-chloro-o-, -m- and -p-methylacetophenone, α-bromo-o-, -m- and -p-methylacetophenone, α-chloro-o-, -m- and -p-methoxyacetophenone, α-bromo-o-, -m- and -p-methoxyacetophenone, α-chloro-o-, -m- and -p-fluoroacetophenone, α-bromo-o-, -m- and -pfluoroacetophenone, α,o-, α,m- and -α-dichloroacetophenone, α-bromo-o-, -m- and -p-chloroacetophenone, α-chloro-o-, -m- and -p-trifluoromethylacetophenone and α-bromo-o-, -m- and -p-trifluoromethylacetophenone.

The reaction of VI and VII is carried out in the absence or—preferably—in the presence of one of the inert solvents or diluents or mixtures mentioned above, at temperatures between about 20° and 150°, preferably 50° and 100°, in particular at the boiling point of the particular solvent. It can be advantageous to add an inorganic base (for example NaH) or an organic base. It is also particularly favourable to carry out the reaction under phase transfer conditions, for example in the system methylenedichloride/water/NaOH/catalyst, particularly suitable catalysts being quaternary ammonium salts, for example tetrabutylammonium iodide.

The compounds of the formula I are also obtainable by reacting compounds 9f the formula VIII with compounds of the formula IX. The compounds of the formula VIII ($R^{17}=A_2N$ or AO) can be obtained from the compounds of the formula VI by reaction with dialkylformamide dialkyl acetales or trialkyl orthoformates; and the compounds of the formula VIII ($R^{17}=HO$) can be obtained therefrom by acid hydrolysis. The compounds of the formula IX are mostly known.

The reaction of VIII with IX is carried out essentially under the same conditions as that of VI with VII.

It is also possible, in a compound of the formula I which is obtainable, for example, by one of the reactions (a), (b), (c) or (d) indicated above, to convert one or more of the radicals $R^1$ to $R^6$ into other radicals $R^1$ to $R^6$.

For example, a hydroxyl group or a primary or secondary amino group can be alkylated or acylated and/or a hydrolysable group, for example an ester, CN or acid amide group can be hydrolysed and/or a COOH group can be esterified and/or amidated and/or a compound which otherwise corresponds to the formula I, but contains one or more reducible groups and/or one or more additional C—C and/or C—N bonds instead of one or more H atoms can be treated with a reducing agent and/or an H atom can be replaced by a Hal atom by halogenation and/or a CN group can be converted by reduction into a CHO group.

A hydroxyl group or a primary or secondary amino group can be converted by treatment with alkylating agents into the corresponding secondary or tertiary amino group. The term "alkylating agent" is to be understood here in a wide sense and also embraces, for example, Ar-alkylating, $R^7R^8N$-alkylating agents. Examples of suitable alkylating agents are compounds of the formulae A-Hal, Ar-alkyl-Hal, AO-alkyl-Hal, ArO-alkyl-Hal, Ar-alkyl-O-alkyl-Hal or $R^7R^8N$-alkyl-Hal (wherein Hal is Cl, Br or I) or corresponding sulphonic acid esters, such as methyl chloride, methyl bromide, methyl iodide, dimethyl sulphate, methyl p-toluenesulphonate, ethyl chloride, ethyl bromide, ethyl iodide, diethyl sulphate, n-propyl chloride, bromide or iodide, benzyl chloride, bromide or iodide, 2-methoxyethyl chloride, 2-phenoxyethyl bromide, 2-benzyloxyethyl iodide or 2-morpholinoethyl chloride. It is also possible to carry out a condensation reaction with aldehydes or ketones with the formation of aldehyde-ammonia compounds or Schiff's bases and to treat them with an alkylating agent, and subsequently to hydrolyse the resulting quaternary salt. For example, a primary amine can be converted by a condensation reaction with benzaldehyde into the N-benzylidene compound and this can be converted by means of an alkyl halide into one of its quaternary salts, which can subsequently be converted into the secondary amine, for example by treatment with aqueous alcohol with the elimination of benzaldehyde. It is also possible to alkylate by means of aldehydes or ketones under reducing conditions, for example in the presence of hydrogen and a hydrogenation catalyst, or in the presence of $NaBH_4$ or $NaCNBH_3$, the corresponding aldehyde-ammonias being formed as intermediate products. For example, one or two methyl groups can be introduced by means of formaldehyde in the presence of formic acid. It is also possible to carry out alkylation in the presence of Raney nickel, using an alcohol having 1–6 C atoms. It is preferable to carry out the alkylation in the presence or absence of one of the inert solvents mentioned, for example DMF, at temperatures between about 0° and about 120°, preferably between 40° and 100°, and it is also possible for a catalyst to be present, preferably a base, such as potassium tert.-butylate or NaH.

Suitable acylating agents for acylating primary or secondary amines of the formula I are preferably the halides (for example chlorides or bromides) or anhydrides of carboxylic acids of the formulae AcOH, for example acetic anhydride, propionyl chloride, isobutyryl bromide, formic/acetic anhydride, benzoyl chloride, p-methoxybenzoyl chloride or phenylacetyl chloride. It is possible, but not necessary, to add a base, such as NaOH, KOH, pyridine or triethylamine, in the course of the acylation. The acylation is preferably carried out in the presence or absence of an inert solvent, for example a hydrocarbon, such as benzene or toluene, a nitrile, such as acetonitrile, an amide, such as DMF, or an excess of a tertiary base, such as pyridine or triethylamine, and at temperatures between about 0° and about 160°, preferably between 20° and 120°. Treating the amines with isocyanates results analogously in the corresponding ureas (for example compounds in which Ar is $R_{11}$NHCONH-phenyl).

Hydrolysable groups in a compound of the formula I can, if desired, be hydrolysed, preferably by treatment with acids, for example $H_2SO_4$, HCl, HBr or $H_3PO_4$, or with bases, for example NaOH, KOH, $Na_2CO_3$ or $K_2CO_3$, in aqueous or partly aqueous solution, it being possible for an additional inert solvent to be present, for example an alcohol, such as methanol, ethanol or isopropanol. The reaction temperatures are between about 0° and about 150°, preferably between 15° and 110°.

Specifically, it is possible, for example, to hydrolyse nitrile groups with 50–80% sulphuric acid to give $CONH_2$ groups or, under more vigorous conditions, for example at higher temperatures, to give COOH groups. The hydrolysis of $CONH_2$ to COOH groups is also advantageously carried out using 50–80% sulphuric acid. Ester groups can be saponified with dilute aqueous-alcoholic NaOH or KOH.

N-acyl groups can be split off with the formation of the free amines by treatment with aqueous-alcoholic bases, for example aqueous-methanolic NaOH at 60°–80°. Phthalimido groups can be split off analogously, but under milder conditions by successive treatment with hydrazine hydrate and alcoholic mineral acid, for example methanolic hydrochloric acid.

COOH groups present in a compound of the formula I can, if desired, be esterified. Alcohols of the formula A—OH and reactive derivatives thereof are suitable for the esterification. Suitable reactive derivatives are, in particular, the corresponding metal alcoholates, preferably the alkali metal alcoholates, for example sodium or potassium alcoholates. It is advantageous to carry out the esterification in the presence of an inert solvent. Solvents which are very suitable are, in particular, ethers, such as diethyl ether, di-n-butyl ether, THF, dioxane or anisole, ketones, such as acetone, butanone or cyclohexanone, amides, such as DMF or phosphoric acid hexamethyltriamide, hydrocarbons, such as benzene, toluene or xylene, halogenated hydrocarbons, such as carbon tetrachloride or tetrachloroethylene, and sulphoxides, such as dimethyl sulphoxide or sulpholane. Water-immiscible solvents can be used advantageously at the same time for removal by azeotropic distillation of the water formed in the esterification. In some cases an excess of an organic base, for example pyridine, quinoline or triethylamine, can also be used as a solvent for the esterification. The esterification can also be carried out in the absence of a solvent, for example merely by heating the components in the presence of sodium acetate. The reaction temperature is usually between −50° and +150°, preferably between −20° and +80°. At these temperatures the esterification reactions are complete after 15 minutes to 48 hours, as a rule. In a specific case, the reaction conditions for the esterification depend largely on the nature of the starting materials used. Thus a free carboxylic acid is usually reacted with a free alcohol in the presence of a strong acid, for example a mineral acid, such as hydrochloric acid or sulphuric acid. A preferred mode of reaction is to react an acid anhydride or, in particular, an acid chloride with an alcohol, preferably in a basic medium, bases of importance being, in particular, alkali metal hydroxides, such as sodium hydroxide or potassium hydroxide, alkali metal carbonates or bicarbonates, such as sodium carbonate, sodium bicarbonate, potassium carbonate or potassium bicarbonate, alkali metal acetates, such as sodium acetate or potassium acetate, alkaline earth metal hydroxides, such as calcium hydroxide, or organic bases, such as triethylamine, pyridine, lutidine, collidine or quinoline. Esterification reactions are carried out under particularly mild conditions by means of the dehydrating agents customary in peptide synthesis, such as dicyclohexylcarbodiimide.

It is also possible to convert carboxylic acids into the corresponding acid halides by means of inorganic acid chlorides or bromides, such as $SOCl_2$ or $PBr_3$, preferably in the presence of an inert solvent, such as DMF, at 0°–30°. The corresponding acid amides can be obtained from these acid halides by reaction with ammonia or amines, preferably in the presence of an inert solvent, such as DMF, at 0°–30°.

It is also possible to reduce reducible groups, for example nitro groups to amino groups, and/or to hydrogenate multiple bonds, for example C—C double bonds. Reduction is effected, for example, by catalytic hydrogenation or by chemical means. Noble metal, nickel or cobalt catalysts, for example, are suitable for catalytic hydrogenations. Suitable noble metals are primarily platinum or palladium, which can be present on supports, such as charcoal or calcium carbonate, as oxides, such as platinum oxide, or in a finely divided form. Preferred catalysts are Pd-on-charcoal and Raney nickel. Hydrogenation is preferably carried out under pressures between 1 and 200, preferably 1 and 10, bar and at temperatures between 0° and 150°, preferably 15° and 60°, in the presence of one of the inert solvents indicated, preferably methanol, ethanol, isopropanol or acetic acid.

It is also possible to replace H atoms by Hal atoms by treating them with halogenating agents. Thus it is possibLe, for example, in compounds of the formula I in which $R^2$ is $CH_3$ to introduce a bromine atom into the methyl group by means of pyridiniumbromide perbromide in an inert solvent, such as methylenedichloride, at temperatures between about $-10°$ and $+30°$, preferably 0° and 10°. 2-bromomethyl-3-alkoxycarbonyl-1,4-dihydropyridines of the formula I which, for example, are obtainable by this route, can readily be hydrolysed to the corresponding lactones I ($R^2$ and $R^3$ together $=-CH_2-O-CO-$), for example by heating for about 0.5–2 hours with moist inert solvents, such as acetonitrile; 2-hydroxymethyl-3-alkoxycarbonyl-1,4-dihydropyridine is formed as a by-product and intermediate product.

It is also possible to convert CN groups into CHO groups by reduction, particularly advantageously by treating the nitriles with Raney nickel in an inert solvent or solvent mixture, for example pyridine/water/acetic acid, at temperatures between about 0° and about 60°, preferably 15° and 30°.

A base of the formula I can be converted into the appropriate acid addition salt by means of an acid. Acids suitable for this reaction are those which afford physiologically acceptable salts. Thus it is possible to use inorganic acids, for example sulphuric acid, nitric acid, hydrogen halide acids, such as hydrochloric acid or hydrobromic acid, phosphoric acids, such as orthophosphoric acid, or sulphamic acid, and also organic acids, especially aliphatic, alicyclic, araliphatic, aromatic or heterocyclic, monobasic or polybasic carboxylic, sulphonic or sulphuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2-phenylpropionic or 3-phenylpropionic acid, citric acid, gluconic acid, ascorbic acid, nicotinic acid, isonicotinic acid, methanesulphonic or ethanesulphonic acid, ethanedisulphonic acid, 2-hydroxyethanesulphonic acid, benzenesulphonic acid, p-toluenesulphonic acid, naphthalenemonosulphonic and naphthalenedisulphonic acids or laurylsulphuric acid. Salts with physiologically unacceptable acids, for example picrates, can be used to isolate or purify the compounds of the formula I.

The free bases of the formula I can, if desired, be liberated from their salts by treatment with strong bases, such as sodium hydroxide or potassium hydroxide or sodium carbonate or potassium carbonate.

On the other hand, compounds of the formula I having free COOH groups can be converted into their metal or ammonium salts by reaction with bases. Suitable salts are, in particular, the sodium, potassium, magnesium, calcium and ammonium salts, and also substituted ammonium salts, for example the dimethylammonium, diethylammonium, monoethanolammonium, diethanolammonium, triethanolammonium, cyclohexylammonium or dicyclohexylammonium salts.

The compounds of the formula I can contain one or more centres of asymmetry. In this case they are usually present in the racemic form. Resulting racemates can be resolved into their optical antipodes mechanically or chemically in accordance with methods which are in themselves known. Preferably, diastereomers are formed from the racemic mixture by reaction with an optically active resolving agent. Examples of suitable resolving agents are optically active acids, such as the D- and L-forms of tartaric acid, diacetyltartaric acid, dibenzoyltartaric acid, mandelic acid, malic acid, lactic acid or the various optically active camphorsulphonic acids, such as $\beta$-camphorsulphonic acid.

It is also possible, of course, to obtain optically active compounds of the formula I in accordance with the methods described above, by using starting materials which are already optically active.

The enantiomeric forms of optically active compounds of the formula I can differ in degree or fundamentally in their pharmacological properties, such as, for example, their calcium-antagonistic or calcium-agonistic action, but they can also be identical.

The invention also relates to the use of the compounds of the formula I and their physiologically acceptable salts for the preparation of pharmaceutical formulations, especially by a non-chemical route. In this regard they can be brought into a suitable dosage form together with at least one solid, liquid and/or semiliquid excipient or auxiliary and, if appropriate, in combination with one or more further active compounds.

The invention also relates to agents, especially pharmaceutical formulations, containing at least one compound of the formula I and/or one of its physiologically acceptable salts.

These formulations can be used as medicaments in human or veterinary medicine. Possible excipients are organic or inorganic substances which are suitable for enteral (for example oral) or parenteral administration or topical application and do not react with the new compounds, for example water, vegetable oils, benzyl alcohols, alkylene glycols, polyethylene glycols, glyceroltriacetate, gelatine, carbohydrates, such as lactose or starch, magnesium stearate, talc or petroleum jelly.

In particular, tablets, pills, coated tablets, capsules, powders, granules, syrups, elixirs or drops are used for oral administration, suppositories are used for rectal administration, solutions, preferably oily or aqueous solutions, and also suspensions, emulsions or implants are used for parenteral administration, while ointments, creams or powders are used for topical application. The new compounds can also be lyophilized and the resulting lyophilisates can be used, for example, for the preparation of injection preparations.

The formulations indicated can be sterilized and/or can contain auxiliaries, such as lubricants, preservatives, stabilizers and/or wetting agents, emulsifiers, salts for controlling the osmotic pressure, buffer substances, colorants, flavouring substances and/or aroma substances. They can, if desired, also contain one or more further active compounds, for example one or more vitamins.

The invention also relates to the use of the compounds of the formula I in combating diseases, in particular cardiac insufficiency, arterial hypertension, coronary sclerosis, atherosclerosis, arrhythmia and, in particular, angina pectoris, and also diseases associated with hypertension, pulmonary hypertension, Raynaud's phenomenon, migraine, asthma, cardiac hypertrophy, ischaemia, myocardial infarction, and also prolonged spasms of internal organs (oesophagus spasms or achalasia), ureteral spasms, incontinence of urine, irritable bladder, premature labour, dysmenorrhoea, intestinal spasms, cerebrovascular circulatory disturbances, vertigo, seasickness, epilepsy, vertebrobasilar insufficiency or endocrinological disorders.

In this regard, the substances according to the invention are usually administered to humans or mammals, such as monkeys, dogs, cats, rats or mice, analogously to known calcium-antagonists, such as verapamil or nifedipine, to humans preferably in dosages between about 5 and 500 mg, especially between 20 and 100 mg, per dosage unit. The daily dose is preferably between about 0.1 and 10, especially between 0.4 and 2, mg/kg of body weight. The particular dose for each specific patient depends, however, on a very wide variety of factors, for example on the effectiveness of the particular compound employed, in the age, body weight, general state of health, sex, diet, the time and means of administration, rate of excretion, combination of medicaments and severity of the particular disease to which the therapy applies. Oral administration is preferred. The foregoing dosage range applies to all the mentioned indications and particularly to cardiac insufficiency and angina pectoris.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the preceding text and the following examples, all temperatures are set forth uncorrected in degrees Celsius and all parts and percentages are by weight; unless otherwise indicated.

"Customary working up" means as follows: if necessary, water and methylenedichloride or ethylacetate are added, the mixture is shaken, the phases are separated, the organic phase is washed with water, dried over $Na_2SO_4$ and evaporated, and the residue is purified by chromatography over silica gel and/or by crystallization.

EXAMPLE 1

A solution of 2.65 g of 2-(o-formylphenyl)-4-phenylthiazole [M.P. 99°-100°; obtainable by reacting o-dimethoxymethylbenzonitrile with $H_2S$ to give o-dimethoxymethylthiobenzamide (M.P. 100°-102°), reacting the latter with α-bromoacetophenone to give o-dimethoxymethylthiobenzoic acid imide S-phenacyl ester (oil), and cyclizing the latter to give 2-(o-dimethoxymethylphenyl)-4-phenylthiazole by boiling with methanol and subsequent hydrolysis with aqueous hydrochloric acid], 1.06 ml of 33% aqueous ammonia, 2.32 g of methyl acetoacetate and 120 ml of methanol is boiled for 18 hours and evaporated. Treating the residue with ether gives 2,6-dimethyl-3,5-dimethoxycarbonyl-4-o-(4-phenyl-2-thiazolyl)-phenyl-1,4-dihydropyridine, M.P. 145°-148° (decomposition).

The following 2,6-dimethyl-3,5-dimethoxycarbonyl-1,4-dihydropyridines are obtained analogously using the corresponding aldehydes:

2,6-dimethyl-3,5-dimethoxycarbonyl-4-o-(2-thiazolyl)-phenyl-1,4-dihydropyridine
2,6-dimethyl-3,5-dimethoxycarbonyl-4-m-(2-thiazolyl)-phenyl-1,4-dihydropyridine
2,6-dimethyl-3,5-dimethoxycarbonyl-4-o-(4-methyl-2-thiazolyl)-phenyl-1,4-dihydropyridine
2,6-dimethyl-3,5-dimethoxycarbonyl-4-m-(4-methyl-2-thiazolyl)-phenyl-1,4-dihydropyridine
2,6-dimethyl-3,5-dimethoxycarbonyl-4-o-(4,5-dimethyl-2-thiazolyl)-phenyl-1,4-dihydropyridine
2,6-dimethyl-3,5-dimethoxycarbonyl-4-m-(4,5-dimethyl-2- thiazolyl)-phenyl-1,4-dihydropyridine
2,6-dimethyl-3,5-dimethoxycarbonyl-4-o-(4-methyl-5-phenyl-2-thiazolyl)-phenyl-1,4-dihydropyridine
2,6-dimethyl-3,5-dimethoxycarbonyl-4-m-(4-methyl-5-phenyl-2-thiazolyl)-phenyl-1,4-dihydropyridine
2,6-dimethyl-3,5-dimethoxycarbonyl-4-o-(4-ethoxycarbonyl-2-thiazolyl)-phenyl-1,4-dihydropyridine
2,6-dimethyl-3,5-dimethoxycarbonyl-4-m-(4-ethoxycarbonyl-2-thiazolyl)-phenyl-1,4-dihydropyridine
2,6-dimethyl-3,5-dimethoxycarbonyl-4-o-(4-ethoxycarbonyl-5-benzyl-2-thiazolyl)-phenyl-1,4-dihydropyridine
2,6-dimethyl-3,5-dimethoxycarbonyl-4-m-(4-ethoxycarbonyl-5-benzyl-2-thiazolyl)-phenyl-1,4-dihydropyridine
2,6-dimethyl-3,5-dimethoxycarbonyl-4-o-(4-ethoxycarbonylmethyl-2-thiazolyl)-phenyl-1,4-dihydropyridine
2,6-dimethyl-3,5-dimethoxycarbonyl-4-m-(4-ethoxycarbonylmethyl-2-thiazolyl)-phenyl-1,4-dihydropyridine
2,6-dimethyl-3,5-dimethoxycarbonyl-4-o-[4-(2-pyridyl)-2-thiazolyl]-phenyl-1,4-dihydropyridine
2,6-dimethyl-3,5-dimethoxycarbonyl-4-m-[4-(2-pyridyl)-2-thiazolyl]-phenyl-1,4-dihydropyridine
2,6-dimethyl-3,5-dimethoxycarbonyl-4-o-[4-(3-pyridyl)-2-thiazolyl]-phenyl-1,4-dihydropyridine
2,6-dimethyl-3,5-dimethoxycarbonyl-4-m-[4-(3-pyridyl)-2-thiazolyl]-phenyl-1,4-dihydropyridine
2,6-dimethyl-3,5-dimethoxycarbonyl-4-o-[4-(4-pyridyl)-2-thiazolyl]-phenyl-1,4-dihydropyridine
2,6-dimethyl-3,5-dimethoxycarbonyl-4-m-[4-(4-pyridyl)-2-thiazolyl]-phenyl-1,4-dihydropyridine 2,6-dimethyl-3,5-dimethoxycarbonyl-4-o-[4-(3-cyano-6-methyl-2-pyridon-5-yl)-2-thiazolyl]-phenyl-1,4-dihydropyridine 2,6-dimethyl-3,5-dimethoxycarbonyl-4-m-[4-(3-cyano-6-methyl-2-pyridon-5-yl)-2-thiazoly]-phenyl-1,4-dihydropyridine 2,6-dimethyl-3,5-dimethoxycarbonyl-4-m-(4-phenyl-2-thiazolyl)-phenyl-1,4-dihydropyridine 2,6-dimethyl-3,5-dimethoxycarbonyl-4-o-(4-phenyl-5-methyl-2-thiazolyl)-phenyl-1,4-dihydropyridine 2,6-dimethyl-3,5-dimethoxycarbonyl-4-m-(4-phenyl-5-methyl-2-thiazolyl)-phenyl-1,4-dihydropyridine 2,6-dimethyl-3,5-dimethoxycarbonyl-4-o-(4-o-tolyl-2-thiazolyl)-phenyl-1,4-dihydropyridine 2,6-dimethyl-3,5-dimethoxycarbonyl-4-m-(4-o-tolyl-2-thiazolyl)-phenyl-1,4-dihydropyridine 2,6-dimethyl-3,5-dimethoxycarbonyl-4-o-(4-m-tolyl-2-thiazolyl)-phenyl-1,4-dihydropyridine M.P. 170°–172°

2,6-dimethyl-3,5-dimethoxycarbonyl-4-m-(4-m-tolyl-2-thiazolyl)-phenyl-1,4-dihydropyridine 2,6-dimethyl-3,5-dimethoxycarbonyl-4-o-(4-p-tolyl-2-thiazolyl)-phenyl-1,4-dihydropyridine M.P. 124°–127° (decomposition)

2,6-dimethyl-3,5-dimethoxycarbonyl-4-m-(4-p-tolyl-2-thiazolyl)-phenyl-1,4-dihydropyridine 2,6-dimethyl-3,5-dimethoxycarbonyl-4-o-[4-(2,4,6-trimethylphenyl)-2-thiazolyl]-phenyl-1,4-dihydropyridine 2,6-dimethyl-3,5-dimethoxycarbonyl-4-m-[4-(2,4,6-trimethylphenyl)-2-thiazolyl]-phenyl-1,4-dihydropyridine 2,6-dimethyl-3,5-dimethoxycarbonyl-4-o-[4-(2,6-dimethyl-4-tert.-butylphenyl)-2-thiazolyl]-phenyl-1,4-dihydropyridine 2,6-dimethyl-3,5-dimethoxycarbonyl-4-m-[4-(2,6-dimethyl-4-tert.-butylphenyl)-2-thiazolyl]-phenyl-1,4-dihydropyridine 2,6-dimethyl-3,5-dimethoxycarbonyl-4-o-(4-o-methoxyphenyl-2-thiazolyl)-phenyl-1,4-dihydropyridine 2,6-dimethyl-3,5-dimethoxycarbonyl-4-m-(4-o-methoxyphenyl-2-thiazolyl)-phenyl-1,4-dihydropyridine 2,6-dimethyl-3,5-dimethoxycarbonyl-4-o-(4-m-methoxyphenyl-2-thiazolyl)-phenyl-1,4-dihydropyridine 2,6-dimethyl-3,5-dimethoxycarbonyl-4-m-(4-m-methoxyphenyl-2-thiazolyl)-phenyl-1,4-dihydropyridine 2,6-dimethyl-3,5-dimethoxycarbonyl-4-o-(4-p-methoxyphenyl-2-thiazolyl)-phenyl-1,4-dihydropyridine M.P. 110°–114° (decomposition)

2,6-dimethyl-3,5-dimethoxycarbonyl-4-m-(4-p-methoxyphenyl-2-thiazolyl)-phenyl-1,4-dihydropyridine 2,6-dimethyl-3,5-dimethoxycarbonyl-4-o-[4-(2,5-dimethoxyphenyl)-2-thiazolyl]-phenyl-1-4-dihydropyridine 2,6-dimethyl-3,5-dimethoxycarbonyl-4-m-[4-(2,5-dimethoxyphenyl)-2-thiazolyl]-phenyl-1,4-dihydropyridine 2,6-dimethyl-3,5-dimethoxycarbonyl-4-o-[4-(3,4-dimethoxyphenyl)-2-thiazolyl]-phenyl-1,4-dihydropyridine 2,6-dimethyl-3,5-dimethoxycarbonyl-4-m-[4-(3,4-dimethoxyphenyl)-2-thiazolyl]-phenyl-1,4-dihydropyridine 2,6-dimethyl-3,5-dimethoxycarbonyl-4-o-[4-(3,4-dimethoxyphenyl)-5-methyl-2-thiazolyl]-phenyl-1,4-dihydropyridine 2,6-dimethyl-3,5-dimethoxycarbonyl-4-m-[4-(3,4-dimethoxyphenyl)-5-methyl-2-thiazolyl]-phenyl-1,4-dihydropyridine 2,6-dimethyl-3,5-dimethoxycarbonyl-4-o-[4-(3,4,5-trimethoxyphenyl)-2-thiazolyl]-phenyl-1,4-dihydropyridine 2,6-dimethyl-3,5-dimethoxycarbonyl-4-m-[4-(3,4,5-trimethoxyphenyl)-2-thiazolyl]-phenyl-1,4-dihydropyridine 2,6-dimethyl-3,5-dimethoxycarbonyl-4-o-(4-p-ethoxyphenyl-2-thiazolyl)-phenyl-1,4-dihydropyridine 2,6-dimethyl-3,5-dimethoxycarbonyl-4-m-(4-p-ethoxyphenyl-2-thiazolyl)-phenyl-1,4-dihydropyridine 2,6-dimethyl-3,5-dimethoxycarbonyl-4-o-(4-o-fluorophenyl-2-thiazolyl)-phenyl-1,4-dihydropyridine 2,6-dimethyl-3,5-dimethoxycarbonyl-4-m-(4-o-fluorophenyl-2-thiazolyl)-phenyl-1,4-dihydropyridine 2,6-dimethyl-3,5-dimethoxycarbonyl-4-o-(4-m-fluorophenyl-2-thiazolyl)-phenyl-1,4-dihydropyridine 2,6-dimethyl-3,5-dimethoxycarbonyl-4-m-(4-m-fluorophenyl-2-thiazolyl)-phenyl-1,4-dihydropyridine 2,6-dimethyl-3,5-dimethoxycarbonyl-4-o-(4-p-fluorophenyl-2-thiazolyl)-phenyl-1,4-dihydropyridine 2,6-dimethyl-3,5-dimethoxycarbonyl-4-m-(4-p-fluorophenyl-2-thiazolyl)-phenyl-1,4-dihydropyridine 2,6-dimethyl-3,5-dimethoxycarbonyl-4-o-(4-o-chlorophenyl-2-thiazolyl)-phenyl-1,4-dihydropyridine 2,6-dimethyl-3,5-dimethoxycarbonyl-4-m-(4-o-chlorophenyl-2-thiazolyl)-phenyl-1,4-dihydropyridine 2,6-dimethyl-3,5-dimethoxycarbonyl-4-o-(4-m-chlorophenyl-2-thiazolyl)-phenyl-1,4-dihydropyridine 2,6-dimethyl-3,5-dimethoxycarbonyl-4-m-(4-m-chlorophenyl-2-thiazolyl)-phenyl-1,4-dihydropyridine 2,6-dimethyl-3,5-dimethoxycarbonyl-4-o-(4-p-chlorophenyl-2-thiazolyl)-phenyl-1,4-dihydropyridine M.P. 206°–208° (decomposition)

2,6-dimethyl-3,5-dimethoxycarbonyl-4-m-(4-p-chlorophenyl-2-thiazolyl)-phenyl-1,4-dihydropyridine 2,6-dimethyl-3,5-dimethoxycarbonyl-4-o-(4-p-chlorophenyl-5-methyl-2-thiazolyl)-phenyl-1,4-dihydropyridine 2,6-dimethyl-3,5-dimethoxycarbonyl-4-m-(4-p-chlorophenyl-5-methyl-2-thiazolyl)-phenyl-1,4-dihydropyridine 2,6-dimethyl-3,5-dimethoxycarbonyl-4-o-[4-(2,4-dichlorophenyl)-2-thiazolyl]-phenyl-1,4-dihydropyridine 2,6-dimethyl-3,5-dimethoxycarbonyl-4-m-[4-(2,4-dichlorophenyl)-2-thiazolyl]-phenyl-1,4-dihydropridine 2,6-dimethyl-3,5-dimethoxycarbonyl-4-o-[4-(3,4-dichlorophenyl)-2-thiazolyl]-phenyl-1,4-dihydropyridine M.P. 108°–110°

2,6-dimethyl-3,5-dimethoxycarbonyl-4-m-[4-(3,4-dichlorophenyl)-2-thiazolyl]-phenyl-1,4-dihydropyridine 2,6-dimethyl-3,5-dimethoxycarbonyl-4-o-(4-p-bromophenyl-2-thiazolyl)-phenyl-1,4-dihydropyridine 2,6-dimethyl-3,5-dimethoxycarbonyl-4-m-(4-p-bromophenyl-2-thiazolyl)-phenyl-1,4-dihydropyridine 2,6-dimethyl-3,5-dimethoxycarbonyl-4-o-[4-(2,4-dimethoxy-5-bromophenyl)-2-thiazolyl]-phenyl-1,4-dihydropyridine 2,6-dimethyl-3,5-dimethoxycarbonyl-4-m-[4-(2,4-dimethoxy-5-bromophenyl)-2-thiazolyl]-phenyl-1,4-dihydropyridine 2,6-dimethyl-3,5-dimethoxycarbonyl-4-o-(4-m-trifluoromethylphenyl-2-thiazolyl)-phenyl-1,4-dihydropyridine 2,6-dimethyl-3,5-dimethoxycarbonyl-4-m-(4-m-trifluoromethylphenyl-2-thiazolyl)-phenyl-1-4-dihydropyridine 2,6-dimethyl-3,5-dimethoxycarbonyl-4-o-(4-o-hydroxyphenyl-2-thiazolyl)-phenyl-1,4-dihydropyridine 2,6-dimethyl-3,5-dimethoxycarbonyl-4-m-(4-o-hydroxyphenyl-2-thiazolyl)-phenyl-1,4-dihydropyridine 2,6-dimethyl-3,5-dimethoxycarbonyl-4-o-(4-m-hydroxyphenyl-2-thiazolyl)-phenyl-1,4-dihydropyridine 2,6-dimethyl-3,5-dimethoxycarbonyl-4-m-(4-m-hydroxyphenyl-2-thiazolyl)-phenyl-1,4-dihydropyridine 2,6-dimethyl-3,5-dimethoxycarbonyl-4-o-(4-p-hydroxyphenyl-2-thiazolyl)-phenyl-1,4-dihydropyridine 2,6-dimethyl-3,5-dimethoxycarbonyl-4-m-(4-p-hydroxyphenyl-2-thiazolyl)-phenyl-1,4-dihydropyridine 2,6-dimethyl-3,5-dimethoxycarbonyl-4-o-[4-(3,4-dihydroxyphenyl)-2-thiazolyl]-phenyl-1,4-dihydropyridine 2,6-dimethyl-3,5-dimethoxycarbonyl-4-m-[4-(3,4-dihydroxyphenyl)-2-thiazolyl]-phenyl-1,4-dihydropyridine 2,6-dimethyl-3,5-dimethoxycarbonyl-4-o-(4-o-nitrophenyl-2-thiazolyl)-phenyl-1,4-dihydropyridine 2,6-dimethyl-3,5-dimethoxycarbonyl-4-m-(4-o-nitrophenyl-2-thiazolyl)-phenyl-1,4-dihydropyridine 2-6-dimethyl-3,5-dimethoxycarbonyl-4-o-(4-m-nitrophenyl-2-thiazolyl)-phenyl-1,4-dihydropyridine 2,6-dimethyl-3,5-dimethoxycarbonyl-4-m-(4-m-nitrophenyl-2-thiazolyl)-phenyl-1,4-dihydropyridine 2,6-dimethyl-3,5-dimethoxycarbonyl-4-o-(4-p-nitrophenyl-2-thiazolyl)-phenyl-1,4-dihydropyridine 2,6-dimethyl-3,5-dimethoxycarbonyl-4-m-(4-p-nitrophenyl-2-thiazolyl)-phenyl-1,4-dihydropyridine 2,6-dimethyl-3,5-dimethoxycarbonyl-4-o-[4-(3-nitro-4-methoxyphenyl)-2-thiazolyl]-phenyl-1,4-dihydropyridine 2,6-dimethyl-3,5-dimethoxycarbonyl-4-m-[4-(3-nitro-4-methoxyphenyl)-2-thiazolyl]-phenyl-1,4-dihydropyridine 2,6-dimethyl-3,5-dimethoxycarbonyl-4-o-(4-p-dimethylaminophenyl-2-thiazolyl)-phenyl-1,4-dihydropyridine 2,6-dimethyl-3,5-dimethoxycarbonyl-4-m-(4-p-dimethylaminophenyl-2-thiazolyl)-phenyl-1,4-dihydropyridine 2,6-dimethyl-3,5-dimethoxycarbonyl-4-o-(4-p-acetamidophenyl-2-thiazolyl)-phenyl-1,4-dihydropyridine 2,6-dimethyl-3,5-dimethoxycarbonyl-4-m-(4-p-acetamidophenyl-2-thiazolyl)-phenyl-1,4-dihydropyridine 2,6-dimethyl-3,5-dimethoxycarbonyl-4-o-[4-(3-acetamido-4-methoxyphenyl)-2-thiazolyl]-phenyl-1,4-dihydropyridine 2,6-dimethyl-3,5-dimethoxycarbonyl-4-m-[4-(3-acetamido-4-methoxyphenyl)-2-thiazolyl]-phenyl-1,4-dihydropyridine 2,6-dimethyl-3,5-dimethoxycarbonyl-4-o-(4-p-cyanophenyl-2-thiazolyl)-phenyl-1,4-dihydropyridine 2,6-dimethyl-3,5-dimethoxycarbonyl-4-m-(4-p-cyanophenyl-2-thiazolyl)-phenyl-1,4-dihydropyridine 2,6-dimethyl-3,5-dimethoxycarbonyl-4-o-(4-p-carbamoylphenyl-2-thiazolyl)-phenyl-1,4-dihydropyridine 2,6-dimethyl-3,5-dimethoxycarbonyl-4-m-(4-p-carbamoylphenyl-2-thiazolyl)-phenyl-1,4-dihydropyridine 2,6-dimethyl-3,5-dimethoxycarbonyl-4-o-(4-o-sulphamoylphenyl-2-thiazolyl)-phenyl-1,4-dihydropyridine 2,6-dimethyl-3,5-dimethoxycarbonyl-4-m-(4-o-sulphamoylphenyl-2-thiazolyl)-phenyl-1,4-dihydropyridine 2,6-dimethyl-3,5-dimethoxycarbonyl-4-o-(4-m-sulphamoylphenyl-2-thiazolyl)-phenyl-1,4-dihydropyridine 2,6-dimethyl-3,5-dimethoxycarbonyl-4-m-(4-m-sulphamoylphenyl-2-thiazolyl)-phenyl-1,4-dihydropyridine 2,6-dimethyl-3,5-dimethoxycarbonyl-4-o-(4-p-sulphamoylphenyl-2-thiazolyl)-phenyl-1,4-dihydropyridine 2,6-dimethyl-3,5-dimethoxycarbonyl-4-m-(4-p-sulphamoylphenyl-2-thiazolyl)-phenyl-1,4-dihydropyridine 2,6-dimethyl-3,5-dimethoxycarbonyl-4-o-(4-p-difluoromethoxyphenyl-2-thiazolyl)-phenyl-1,4-dihydropyridine 2,6-dimethyl-3,5-dimethoxycarbonyl-4-m-(4-p-difluoromethoxyphenyl-2-thiazolyl)-phenyl-1,4-dihydropyridine 2,6-dimethyl-3,5-dimethoxycarbonyl-4-o-[4-(4-diphenylyl)-2-thiazolyl]-phenyl-1,4-dihydropyridine 2,6-dimethyl-3,5-dimethoxycarbonyl-4-m-[4-(4-diphenylyl)-2-thiazolyl]-phenyl-1,4-dihydropyridine 2,6-dimethyl-3,5-dimethoxycarbonyl-4-o-(4-p-phenoxyphenyl-2-thiazolyl)-phenyl-1,4-dihydropyridine 2,6-dimethyl-3,5-dimethoxycarbonyl-4-m-(4-p-phenoxyphenyl-2-thiazolyl)-phenyl-1,4-dihydropyridine

EXAMPLE 2

The following 2,6-dimethyl-3,5-diethoxycarbonyl-1,4-dihydropyridines are obtained analogously to Example 1 using ethyl acetoacetate:

2,6-dimethyl-3,5-diethoxycarbonyl-4-o-(2-thiazolyl)-phenyl-1,4-dihydropyridine 2,6-dimethyl-3,5-diethoxycarbonyl-4-m-(2-thiazolyl)-phenyl-1,4-dihydropyridine 2,6-dimethyl-3,5-diethoxycarbonyl-4-o-(4-methyl-2-thiazolyl)phenyl-1,4-dihydropyridine 2,6-dimethyl-3,5-diethoxycarbonyl-4-m-(4-methyl-2-thiazolyl)phenyl-1,4-dihydropyridine 2,6-dimethyl-3,5-diethoxycarbonyl-4-o-(4,5-dimethyl-2-thiazoly)-phenyl-1,4-dihydropyridine 2,6-dimethyl-3,5-diethoxycarbonyl-4-m-(4,5-dimethyl-2- thiazolyl)-phenyl-1,4-dihydropyridine 2,6-dimethyl-3,5-diethoxycarbonyl-4-o-(4-methyl-5-phenyl-2-thiazolyl)-phenyl-1,4-dihydropyridine
2,6-dimethyl-3,5-diethoxycarbonyl-4-m-(4-methyl-5-phenyl-2-thiazolyl)-phenyl-1,4-dihydropyridine
2,6-dimethyl-3,5-diethoxycarbonyl-4-o-(4-ethoxycarbonyl-2-thiazolyl)-phenyl-1,4-dihydropyridine
2,6-dimethyl-3,5-diethoxycarbonyl-4-m-(4-ethoxycarbonyl-2-thiazolyl)-phenyl-1,4-dihydropyridine
2,6-dimethyl-3,5-diethoxycarbonyl-4-o-(4-ethoxycarbonyl-5-benzyl-2-thiazolyl)-phenyl-1,4-dihydropyridine
2,6-dimethyl-3,5-diethoxycarbonyl-4-m-(4-ethoxycarbonyl-5-benzyl-2-thiazolyl)-phenyl-1,4-dihydropyridine
2,6-dimethyl-3,5-diethoxycarbonyl-4-o-(4-ethoxycarbonylmethyl-2-thiazolyl)-phenyl-1,4-dihydropyridine
2,6-dimethyl-3,5-diethoxycarbonyl-4-m-(4-ethoxycarbonylmethyl-2-thiazolyl)-phenyl-1,4-dihydropyridine
2,6-dimethyl-3,5-diethoxycarbonyl-4-o-[4-(2-pyridyl)-2-thiazolyl]-phenyl-1,4-dihydropyridine
2,6-dimethyl-3,5-diethoxycarbonyl-4-m-[4-(2-pyridyl)-2-thiazolyl]-phenyl-1,4-dihydropyridine
2,6-dimethyl-3,5-diethoxycarbonyl-4-o-[4-(3-pyridyl)-2-thiazolyl]-phenyl-1,4-dihydropyridine
2,6-dimethyl-3,5-diethoxycarbonyl-4-m-[4-(3-pyridyl)-2-thiazolyl]-phenyl-1,4-dihydropyridine
2,6-dimethyl-3,5-diethoxycarbonyl-4-o-[4-(4-pyridyl)-2thiazolyl]-phenyl-1,4-dihydropyridine
2,6-dimethyl-3,5-diethoxycarbonyl-4-m-[4-pyridyl)-2thiazolyl]-phenyl-1,4-dihydropyridine
2,6-dimethyl-3,5-diethoxycarbonyl-4-o-[4-(3-cyano-6-methyl-2-pyridon-5-yl)-2-thiazolyl]-phenyl-1,4-dihydropyridine
2,6-dimethyl-3,5-diethoxycarbonyl-4-m-[4-(3-cyano-6-methyl-2-pyridon-5-yl)-2-thiazolyl]-phenyl-1,4-dihydropyridine
2,6-dimethyl-3,5-diethoxycarbonyl-4-o-(4-phenyl-2-thiazolyl)-phenyl-1,4-dihydropyridine
2,6-dimethyl-3,5-diethoxycarbonyl-4-m-(4-phenyl-2-thiazolyl)-phenyl-1,4-dihydropyridine
2,6-dimethyl-3,5-diethoxycarbonyl-4-o-(4-phenyl-5-methyl-2-thiazolyl)-phenyl-1,4-dihydropyridine
2,6-dimethyl-3,5-diethoxycarbonyl-4-m-(4-phenyl-5-methyl-2-thiazolyl)-phenyl-1,4-dihydropyridine
2,6-dimethyl-3,5-diethoxycarbonyl-4-o-(4-o-tolyl-2-thiazolyl)-phenyl-1,4-dihydropyridine
2,6-dimethyl-3,5-diethoxycarbonyl-4-m-(4-o-tolyl-2-thiazolyl)-phenyl-1,4-dihydropyridine
2,6-dimethyl-3,5-diethoxycarbonyl-4-o-(4-m-tolyl-2-thiazolyl)-phenyl-1,4-dihydropyridine M.P. 144°–146°
2,6-dimethyl-3,5-diethoxycarbonyl-4-m-(4-m-tolyl-2-thiazolyl)-phenyl-1,4-dihydropyridine
2,6-dimethyl-3,5-diethoxycarbonyl-4-o-(4-p-tolyl-2-thiazolyl)-phenyl-1,4-dihydropyridine
2,6-dimethyl-3,5-diethoxycarbonyl-4-m-(4-p-tolyl-2-thiazolyl)-phenyl-1,4-dihydropyridine
2,6-dimethyl-3,5-diethoxycarbonyl-4-o-[4-(2,4,6-trimethylphenyl)-2-thiazolyl]-phenyl-1,4-dihydropyridine
2,6-dimethyl-3,5-diethoxycarbonyl-4-m-[4-(2,4,6-trimethylphenyl)-2-thiazolyl]-phenyl-1,4-dihydropyridine
2,6-dimethyl-3,5-diethoxycarbonyl-4-o-[4-(2,6-dimethyl-4-tert.-butylphenyl)-2-thiazolyl]-phenyl-1,4-dihydropyridine
2,6-dimethyl-3,5-diethoxycarbonyl-4-m-[4-(2,6-dimethyl-4-tert.-butylphenyl)-2-thiazolyl]-phenyl-1,4-dihydropyridine
2,6-dimethyl-3,5-diethoxycarbonyl-4-o-(4-o-methoxyphenyl-2-thiazolyl)-phenyl-1,4-dihydropyridine
2,6-dimethyl-3,5-diethoxycarbonyl-4-m-(4-o-methoxyphenyl-2-thiazolyl)-phenyl-1,4-dihydropyridine
2,6-dimethyl-3,5-diethoxycarbonyl-4-o-(4-m-methoxyphenyl-2-thiazolyl)-phenyl-1,4-dihydropyridine
2,6-dimethyl-3,5-diethoxycarbonyl-4-m-(4-m-methoxyphenyl-2-thiazolyl)-phenyl-1,4-dihydropyridine
2,6-dimethyl-3,5-diethoxycarbonyl-4-o-(4-p-methoxyphenyl-2-thiazolyl)-phenyl-1,4-dihydropyridine M.P. 184°–186°
2,6-dimethyl-3,5-diethoxycarbonyl-4-m-(4-p-methoxyphenyl-2-thiazolyl)-phenyl-1,4-dihydropyridine
2,6-dimethyl-3,5-diethoxycarbonyl-4-o-[4-(2,5-dimethoxyphenyl)-2-thiazolyl]-phenyl-1,4-dihydropyridine
2,6-dimethyl-3,5-diethoxycarbonyl-4-m-[4-(2,5-dimethoxyphenyl)-2-thiazolyl]-phenyl-1,4-dihydropyridine
2,6-dimethyl-3,5-diethoxycarbonyl-4-o-[4-(3,4-dimethoxyphenyl)-2-thiazolyl]-phenyl-1,4-dihydropyridine
2,6-dimethyl-3,5-diethoxycarbonyl-4-m-[4-(3,4-dimethoxyphenyl)-2-thiazolyl]-phenyl-1,4-dihydropyridine
2,6-dimethyl-3,5-diethoxycarbonyl-4-o-[4-(3,4-dimethoxyphenyl)-5-methyl-2-thiazolyl]-phenyl-1,4-dihydropyridine
2,6-dimethyl-3,5-diethoxycarbonyl-4-m-[4-(3,4-dimethoxyphenyl)-5-methyl-2-thiazolyl]-phenyl-1,4-dihydropyridine
2,6-dimethyl-3,5-diethoxycarbonyl-4-o-[4-(3,4,5-trimethoxyphenyl)-2-thiazolyl]-phenyl-1,4-dihydropyridine
2,6-dimethyl-3,5-diethoxycarbonyl-4-m-[4-(3,4,5-trimethoxyphenyl)-2-thiazolyl]-phenyl-1,4-dihydropyridine
2,6-dimethyl-3,5-diethoxycarbonyl-4-o-(4-p-ethoxyphenyl-2-thiazolyl)-phenyl-1,4-dihydropyridine
2,6-dimethyl-3,5-diethoxycarbonyl-4-m-(4-p-ethoxyphenyl-2-thiazolyl)-phenyl-1,4-dihydropyridine
2,6-dimethyl-3,5-diethoxycarbonyl-4-o-(4-o-fluorophenyl-2-thiazolyl)-phenyl-1,4-dihydropyridine
2,6-dimethyl-3,5-diethoxycarbonyl-4-m-(4-o-fluorophenyl-2-thiazolyl)-phenyl-1,4-dihydropyridine
2,6-dimethyl-3,5-diethoxycarbonyl-4-o-(4-m-fluorophenyl-2-thiazolyl)-phenyl-1,4-dihydropyridine
2,6-dimethyl-3,5-diethoxycarbonyl-4-m-(4-m-fluorophenyl-2-thiazolyl)-phenyl-1,4-dihydropyridine
2,6-dimethyl-3,5-diethoxycarbonyl-4-o-(4-p-fluorophenyl-2-thiazolyl)-phenyl-1,4-dihydropyridine
2,6-dimethyl-3,5-diethoxycarbonyl-4-m-(4-p-fluorophenyl-2-thiazolyl)-phenyl-1,4-dihydropyridine
2,6-dimethyl-3,5-diethoxycarbonyl-4-o-(4-o-chlorophenyl-2-thiazolyl-phenyl-1,4-dihydropyridine
2,6-dimethyl-3,5-diethoxycarbonyl-4-m-(4-o-chlorophenyl-2-thiazolyl)-phenyl-1,4-dihydropyridine
2,6-dimethyl-3,5-diethoxycarbonyl-4-o-(4-m-chlorophenyl-2-thiazolyl)-phenyl-1,4-dihydropyridine
2,6-dimethyl-3,5-diethoxycarbonyl-4-m-(4-m-chlorophenyl-2-thiazolyl)-phenyl-1,4-dihydropyridine
2,6-dimethyl-3,5-diethoxycarbonyl-4-o-(4-p-chlorophenyl-2-thiazolyl)-phenyl-1,4-dihydropyridine 2,6-dimethyl-3,5-diethoxycarbonyl-4-m-(4-p-chlorophenyl-2-thiazolyl)-phenyl-1,4-dihydropyridine 2,6-dimethyl-3,5-diethoxycarbonyl-4-o-(4-p-chlorophenyl-5-methyl-2-thiazolyl)-phenyl-1,4-dihydropyridine 2,6-dimethyl-3,5-diethoxycarbonyl-4-m-(4-p-chlorophenyl-5-methyl-2-thiazolyl)-phenyl-1,4-dihydropyridine 2,6-dimethyl-3,5-diethoxycarbonyl-4-o-[4-(2,4-dichlorophenyl)-2-thiazolyl]-phenyl-1,4-dihydropyridine 2,6-dimethyl-3,5-diethoxycarbonyl-4-m-[4-(2,4-dichlorophenyl)-2-thiazolyl]-phenyl-1,4-dihydropyridine 2,6-dimethyl-3,5-diethoxycarbonyl-4-o-[4-(3,4-dichlorophenyl)-2-thiazolyl]-phenyl-1,4-dihydropyridine M.P. 228°–232° (decomposition)

2,6-dimethyl-3,5-diethoxycarbonyl-4-m-[4-(3,4-dichlorophenyl)-2-thiazolyl]-phenyl-1,4-dihydropyridine 2,6-dimethyl-3,5-diethoxycarbonyl-4-o-(4-p-bromophenyl-2-thiazolyl)-phenyl-1,4-dihydropyridine 2,6-dimethyl-3,5-diethoxycarbonyl-4-m-(4-p-bromophenyl-2-thiazolyl)-phenyl-1,4-dihydropyridine 2,6-dimethyl-3,5-diethoxycarbonyl-4-o-[4-(2,4-dimethoxy-5-bromophenyl)-2-thiazolyl]-phenyl-1,4-dihydropyridine 2,6-dimethyl-3,5-diethoxycarbonyl-4-m-[4-(2,4-dimethoxy-5-bromophenyl)-2-thiazolyl]-phenyl-1,4-dihydropyridine 2,6-dimethyl-3,5-diethoxycarbonyl-4-o-(4-m-trifluoromethylphenyl-2-thiazolyl)-phenyl-1,4-dihydropyridine 2,6-dimethyl-3,5-diethoxycarbonyl-4-m-(4-m-trifluoromethylphenyl-2-thiazolyl)-phenyl-1,4-dihydropyridine 2,6-dimethyl-3,5-diethoxycarbonyl-4-o-(4-o-hydroxyphenyl-2-thiazolyl)-phenyl-1,4-dihydropyridine 2,6-dimethyl-3,5-diethoxycarbonyl-4-m-(4-o-hydroxyphenyl-2-thiazolyl)-phenyl-1,4-dihydropyridine 2,6-dimethyl-3,5-diethoxycarbonyl-4-o-(4-m-hydroxyphenyl-2-thiazolyl)-phenyl-1,4-dihydropyridine 2,6-dimethyl-3,5-diethoxycarbonyl-4-m-(4-m-hydroxyphenyl-2-thiazolyl)-phenyl-1,4-dihydropyridine 2,6-dimethyl-3,5-diethoxycarbonyl-4-o-(4-p-hydroxyphenyl-2-thiazolyl)-phenyl-1,4-dihydropyridine 2,6-dimethyl-3,5-diethoxycarbonyl-4-m-(4-p-hydroxyphenyl-2-thiazolyl)-phenyl-1,4-dihydropyridine 2,6-dimethyl-3,5-diethoxycarbonyl-4-o-[4-(3,4-dihydroxyphenyl)-2-thiazolyl]-phenyl-1,4-dihydropyridine 2,6-dimethyl-3,5-diethoxycarbonyl-4-m-[4-(3,4-dihydroxyphenyl)-2-thiazolyl]-phenyl-1,4-dihydropyridine 2,6-dimethyl-3,5-diethoxycarbonyl-4-o-(4-o-nitrophenyl-2-thiazolyl]-phenyl-1,4-dihydropyridine 2,6-dimethyl-3,5-diethoxycarbonyl-4-m-(4-o-nitrophenyl-2-thiazolyl)-phenyl-1,4-dihydropyridine 2,6-dimethyl-3,5-diethoxycarbonyl-4-o-(4-m-nitrophenyl-2-thiazolyl)-phenyl-1,4-dihydropyridine 2,6-dimethyl-3,5-diethoxycarbonyl-4-m-(4-m-nitrophenyl-2-thiazolyl)-phenyl-1,4-dihydropyridine 2,6-dimethyl-3,5-diethoxycarbonyl-4-o-(4-p-nitrophenyl-2-thiazolyl)-phenyl-1,4-dihydropyridine 2,6-dimethyl-3,5-diethoxycarbonyl-4-m-(4-p-nitrophenyl-2-thiazolyl)-phenyl-1,4-dihydropyridine 2,6-dimethyl-3,5-diethoxycarbonyl-4-o-[4-(3-nitro-4-methoxyphenyl)-2-thiazolyl]-phenyl-1,4-dihydropyridine 2,6-dimethyl-3,5-diethoxycarbonyl-4-m-[4-(3-nitro-4-methoxyphenyl)-2-thiazolyl]-phenyl-1,4-dihydropyridine 2,6-dimethyl-3,5-diethoxycarbonyl-4-o-(4-p-dimethylaminophenyl-2-thiazolyl)-phenyl-1,4-dihydropyridine 2,6-dimethyl-3,5-diethoxycarbonyl-4-m-(4-p-dimethylaminophenyl-2-thiazolyl)-phenyl-1,4-dihydropyridine 2,6-dimethyl-3,5-diethoxycarbonyl-4-o-(4-p-acetamidophenyl-2-thiazolyl)-phenyl-1,4-dihydropyridine 2,6-dimethyl-3,5-diethoxycarbonyl-4-m-(4-p-acetamidophenyl-2-thiazolyl)-phenyl-1,4-dihydropyridine 2,6-dimethyl-3,5-diethoxycarbonyl-4-o-[4-(3-acetamido-4-methoxyphenyl)-2-thiazolyl]-phenyl-1,4-dihydropyridine 2,6-dimethyl-3,5-diethoxycarbonyl-4-m-[4-(3-acetamido-4-methoxyphenyl)-2-thiazolyl]-phenyl-1,4-dihydropyridine 2,6-dimethyl-3,5-diethoxycarbonyl-4-o-(4-p-cyanophenyl-2-thiazolyl)-phenyl-1,4-dihydropyridine 2,6-dimethyl-3,5-diethoxycarbonyl-4-m-(4-p-cyanophenyl-2-thiazolyl)-phenyl-1,4-dihydropyridine 2,6-dimethyl-3,5-diethoxycarbonyl-4-o-(4-p-carbamoylphenyl-2-thiazolyl)-phenyl-1,4-dihydropyridine 2,6-dimethyl-3,5-diethoxycarbonyl-4-m-(4-p-carbamoylphenyl-2-thiazolyl)-phenyl-1,4-dihydropyridine 2,6-dimethyl-3,5-diethoxycarbonyl-4-o-(4-o-sulphamoylphenyl-2-thiazolyl)-phenyl-1,4-dihydropyridine 2,6-dimethyl-3,5-diethoxycarbonyl-4-m-(4-o-sulphamoylphenyl-2-thiazolyl)-phenyl-1,4-dihydropyridine 2,6-dimethyl-3,5-diethoxycarbonyl-4-o-(4-m-sulphamoylphenyl-2-thiazolyl)-phenyl-1,4-dihydropyridine 2,6-dimethyl-3,5-diethoxycarbonyl-4-m-(4-m-sulphamoylphenyl-2-thiazolyl)-phenyl-1,4-dihydropyridine 2,6-dimethyl-3,5-diethoxycarbonyl-4-o-(4-p-sulphamoylphenyl-2-thiazolyl)-phenyl-1,4-dihydropyridine 2,6-dimethyl-3,5-diethoxycarbonyl-4-m-(4-p-sulphamoylphenyl-2-thiazolyl)-phenyl-1,4-dihydropyridine 2,6-dimethyl-3,5-diethoxycarbonyl-4-o-(4-p-difluoromethoxyphenyl-2-thiazolyl)-phenyl-1,4-dihydropyridin 2,6-dimethyl-3,5-diethoxycarbonyl-4-m-(4-p-difluoromethoxyphenyl-2-thiazolyl)-phenyl-1,4-dihydropyridin 2,6-dimethyl-3,5-diethoxycarbonyl-4-o-[4-(4-diphenylyl)-2-thiazolyl]-phenyl-1,4-dihydropyridine 2,6-dimethyl-3,5-diethoxycarbonyl-4-m-[4-(4-diphenylyl)-2-thiazolyl]-phenyl-1,4-dihydropyridine 2,6-dimethyl-3,5-dimethoxycarbonyl-4-o-(4-p-phenoxyphenyl-2-thiazolyl)-phenyl-1,4-dihydropyridine 2,6-dimethyl-3,5-dimethoxycarbonyl-4-m-(4-p-phenoxyphenyl-2-thiazolyl)-phenyl-1,4-dihydropyridine

EXAMPLE 3

A solution of 4.07 g of ethyl 2-acetyl-o-(4-p-methoxyphenyl-2-thiazolyl)-cinnamate [cis-trans mixture; obtainable from 2-o-formylphenyl-4-p-methoxyphenylthiazole and ethyl acetoacetate], 0.7 ml of 33% aqueous ammonia and 1.3 g of ethyl acetoacetate in 40 ml of methanol is heated at the boil for 24 hours and worked up analogously to Example 1 to give 2,6-dimethyl-3,5-diethoxycarbonyl-4-o-(4-p-methoxyphenyl-2-thiazolyl)-phenyl-1,4-dihydropyridine, M.P. 184°–186°.

The following 2,6-dimethyl-4-o-(4-p-methoxyphenyl-2-thiazolyl)-phenyl-1,4-dihydropyridines are obtained analogously using the corresponding keto esters:

2,6-dimethyl-3-methoxycarbonyl-5-ethoxycarbonyl-4-o-(4-p-methoxyphenyl-2-thiazolyl)-phenyl-1,4-dihydropyridine 2,6-dimethyl-3-methoxycarbonyl-5-isopropoxycarbonyl-4-o-(4-p-methoxyphenyl-2-thiazolyl)-phenyl-1,4-dihydropyridine 2,6-dimethyl-3-methoxycarbonyl-5-isobutoxycarbonyl-4-o-(4-p-methoxyphenyl-2-thiazolyl)-phenyl-1,4-dihydropyridine 2,6-dimethyl-3-methoxycarbonyl-5-(2-N-benzyl-N-methylamino-ethoxycarbonyl)-4-o-(4-p-methoxyphenyl-2-thiazolyl)-phenyl-1,4-dihydropyridine 2,6-dimethyl-3-propoxycarbonyl-5-(2-propoxyethoxycarbonyl)-4-o-(4-p-methoxyphenyl-2-thiazolyl)-phenyl-1,4-dihydropyridine 2,6-dimethyl-3-isopropoxycarbonyl-5-(2-methoxyethoxycarbonyl)-4-o-(4-p-methoxyphenyl-2-thiazolyl)-phenyl-1,4-dihydropyridine

EXAMPLE 4

(a) 2-Acetoxymethyl-3,5-diethoxycarbonyl-4-o-(4-phenyl-2-thiazolyl)-phenyl-6-methyl-1,4-dihydropyridine, an oil, is obtained analogously to Example 3 from ethyl 2-acetyl-o-(4-phenyl-2-thiazolyl)-cinnamate, ethyl 4-acetoxy-3-oxobutanoate and ammonia.

(b) 1 g of the compound obtained in (a) is boiled for 1 hour with 15 ml of dioxane saturated with HCl, the mixture is evaporated and the residue is chromatographed to give 2-methyl-3-ethoxycarbonyl-4-o-(4-phenyl-2-thiazolyl)-phenyl-5-oxo-1,4,5,7-tetrahydrofuro[3,4-b]pyridine.

EXAMPLE 5

2-Methyl-3-ethoxycarbonyl-4-o-(4-phenyl-2-thiazolyl)-phenyl-5-oxo-1,4,5,7-tetrahydrofuro[3,4-b]pyridine is obtained analogously to Example 3 from ethyl 2-acetyl-o-(4-phenyl-2-thiazolyl)-cinnamate, tetronic acid (or methyltetronate) and ammonia.

EXAMPLE 6

(a) 2-Methyl-3,5-diethoxycarbonyl-4-o-(4-phenyl-2-thiazolyl)-phenyl-6-ethylenedioxymethyl-1,4-dihydropyridine is obtained analogously to Example 3 from ethyl 2-acetyl-o-(4-phenyl-2-thiazolyl)-cinnamate, ethyl 3-oxo-4,4-ethylenedioxybutyrate and ammonia.

(b) The product obtained in (a) (1 g) is boiled with 50 ml of 10% methanolic hydrochloric acid (monitored by thin layer chromatography). 2-Methyl-3,5-diethoxycarbonyl-4-o-(4-phenyl-2-thiazolyl)-phenyl-6-formyl-1,4-dihydropyridine is obtained.

EXAMPLE 7

A solution of 4.07 g of ethyl 2-acetyl-o-(4-p-methoxyphenyl-2-thiazolyl)-cinnamate and 1.29 g of methyl 3-methylaminocrotonate in 50 ml of ethanol is heated at the boil for 16 hours and evaporated, and the residue is chromatographed over silica gel to give 1,2,6-trimethyl-3-methoxycarbonyl-4-o-(4-p-methoxyphenyl-2-thiazolyl)-phenyl-5-ethoxycarbonyl-1,4-dihydropyridine.

2,6-Dimethyl-3-ethoxycarbonyl-4-o-(4-p-methoxyphenyl-2-thiazolyl)-phenyl-5-cyano-1,4-dihydropyridine is obtained analogously using 3-aminocrotonitrile.

EXAMPLE 8

A mixture of 4.07 g of ethyl 2-acetyl-o-(4-p-methoxyphenyl-2-thiazolyl)-cinnamate and 1 g of tetronamide (cf. German Offenlegungsschrift No. 3,311,003) in 80 ml of methanol is boiled for 24 hours and evaporated. Chromatographing the residue over silica gel gives 2-methyl-3-ethoxycarbonyl-4-o-(4-p-methoxyphenyl-2-thiazolyl)-phenyl-5-oxo-1,4,5,7-tetrahydrofuro[3,4-b]pyridine.

1.87 g of ethyl 3-amino-4-acetoxycrotonate can also be used instead of the tetronamide.

The same product can be obtained analogously from equimolar amounts of (a) 2-o-formylphenyl-4-p-methoxyphenylthiazole, ethyl 4-chloro-3-oxobutyrate and ethyl 3-aminocrotonate, (b) 2-o-formylphenyl-4-p-methoxyphenylthiazole, ethyl 4-acetoxy-3-aminocrotonate and ethyl acetoacetate, the crude 2-methyl-3,5-diethoxycarbonyl-4-o-(4-p-methoxyphenyl-2-thiazolyl)-phenyl-6-acetoxymethyl-1,4-dihydropyridine initially obtained being split, however, by boiling with HCl in dioxane for 45 minutes to give the 6-hydroxymethyl compound, which is lactonized, (c) 2-o-formylphenyl-4-p-methoxyphenylthiazole, ethyl 4-acetoxy-3-oxobutyrate and ethyl 3-aminocrotonate (procedure as in (b)), and (d) ethyl 2-bromoacetyl-o-(4-p-methoxyphenyl-2-thiazole)-cinnamate and ethyl 3-aminocrotonate.

EXAMPLE 9

A solution of 2.95 g of 2-o-formylphenyl-4-p-methoxyphenylthiazole, 2.6 g of ethyl acetoacetate and 0.1 ml of piperidine in 30 ml of isopropanol is boiled for 10 hours. The mixture is cooled and 0.7 ml of 33% aqueous ammonia is added to the resulting solution of 3,5-diethoxycarbonyl-4-o-(4-p-methoxyphenyl-2-thiazole)-phenyl-2,6-heptane dione, which is boiled for a further 6 hours and evaporated, and chromatographing the residue over silica gel gives 2,6-dimethyl-3,5-diethoxycarbonyl-4-o-(4-p-methoxyphenyl-2-thiazolyl)-phenyl-1,4-dihydropyridine, M.P. 184°–186°.

EXAMPLE 10

A solution of 2.65 g of 2-o-formylphenyl-4-phenylthiazole, 1.03 g of nitroacetone and 1.15 g of methyl 3-aminocrotonate in 30 ml of ethanol is boiled for 3 hours and evaporated. Chromatographing the residue over silica gel (98:2 $CH_2Cl_2$$CH_3OH$) gives 2,6-dimethyl-3-methoxycarbonyl-4-o-(4-phenyl-2-thiazolyl)-phenyl-5-nitro-1,4-dihydropyridine.

EXAMPLE 11

A solution of 2.79 g of 2-o-formylphenyl-4-mtolylthiazole, 1.29 g of ethyl 3-aminocrotonate and 1.44 g of ethyl 3-methoxycrotonate in 40 ml of acetonitrile is boiled for 16 hours and evaporated. Chromatographing the residue over silica gel gives 2,6-dimethyl-3,5-diethoxycarbonyl-4-o-(4-m-tolyl-2-thiazolyl)-phenyl-1,4-dihy M.P. 144-146o

EXAMPLE 12

A solution of 2.79 g of 2-o-formylphenyl-4-m-tolyl-thiazole, 1.29 g of ethyl 3-aminocrotonate and 1.44 g of ethyl 3-methoxycrotonate in 40 ml of acetontrile is boiled for 16 hours and evaporated. Chromatographing the residue over silica gel gives 2,6-dimethyl-3,5-diethoxycarbonyl-4-o-(4-m-tolyl-2-thiazolyl)-phenyl-1,4-dihydropyridine, M.P. 144°–146°.

EXAMPLE 12

A solution of 2.79 g of 2-o-formylphenyl-4-m-tolyl-thiazole, 1.30 g of ethyl acetoacetate, 1.44 g of ethyl 3-methoxycrotonate and 0.7 ml of 33% aqueous ammonia in 50 ml of ethanol is boiled for 16 hours and evaporated. Chromatographing over silica gel gives 2,6-dimethyl-3,5-diethoxycarbonyl-4-o-(4-m-tolyl-2-thiazolyl)-phenyl-1,4-dihydropyridine, M.P. 144°–146°.

EXAMPLE 13

A suspension of 3.75 g of 2,6-dimethyl-3,5-dimethoxycarbonyl-4-o-thioureidophenyl-1,4-dihydropyridine [M.P. 230° (decomposition); obtainable by reacting 2,6-dimethyl-3,5-dimethoxycarbonyl-4-o-aminophenyl-1,4-dihydropyridine with benzoyl chloride/NaSCN in acetone at 20° to give the 4-o-(N'-benzoylthioureido)-phenyl compound (M.P. 203°–206° (decomposition)) and splitting off the benzoyl group with K$_2$CO$_3$ in CH$_3$OH/water at 20°] in 150 ml of ethanol is boiled with 1.85 g of 2'-chloroacetophenone for 30 minutes. After cooling, the resulting 2,6-dimethyl-3,5-dimethoxycarbonyl-4-o-(4-phenyl-2-thiazolylamino)-phenyl-1,4-dihydropyridine hydrochloride is filtered off. M.P. 242°–243° (decomposition).

The following 2,6-dimethyl-3,5-dimethoxycarbonyl-1,4-dihydropyridines are obtained analogously using the corresponding chlorocarbonyl or bromocarbonyl compounds of the formula VII:

2,6-dimethyl-3,5-dimethoxycarbonyl-4-o-(2-thiazolylamino)-phenyl-1,4-dihydropyridine, hydrochloride, M.P. 228°–229°

2,6-dimethyl-3,5-dimethoxycarbonyl-4-m-(2-thiazolylamino)-phenyl-1,4-dihydropyridine 2,6-dimethyl-3,5-dimethoxycarbonyl-4-o-(4-methyl-2-thiazolylamino)-phenyl-1,4-dihydropyridine 2,6-dimethyl-3,5-dimethoxycarbonyl-4-m-(4-methyl-2-thiazolylamino)-phenyl-1,4-dihydropyridine 2,6-dimethyl-3,5-dimethoxycarbonyl-4-o-(4,5-dimethyl-2-thiazolylamino)-phenyl-1,4-dihydropyridine, hydrochloride, M.P. 209°

2,6-dimethyl-3,5-dimethoxycarbonyl-4-m-(4,5-dimethyl-2-thiazolylamino)-phenyl-1,4-dihydropyridine 2,6-dimethyl-3,5-dimethoxycarbonyl-4-o-(4-methyl-5-phenyl-2-thiazolylamino)-phenyl-1,4-dihydropyridine, hydrobromide, M.P. 227° (decomposition)

2,6-dimethyl-3,5-dimethoxycarbonyl-4-m-(4-methyl-5-phenyl-2-thiazolylamino)-phenyl- 1,4-dihydropyridine 2,6-dimethyl-3,5-dimethoxycarbonyl-4-o-(4-ethoxycarbonyl-2-thiazolylamino)-phenyl-1,4-dihydropyridine, hydrobromide, M.P. 180°–181°

2,6-dimethyl-3,5-dimethoxycarbonyl-4-m-(4-ethoxycarbonyl-2-thiazolylamino)-phenyl-1,4-dihydropyridine 2,6-dimethyl-3,5-dimethoxycarbonyl-4-o-(4-ethoxycarbonyl-5-benzyl-2-thiazolylamino)-phenyl-1,4-dihydropyridine, M.P. 200°–204°

2,6-dimethyl-3,5-dimethoxycarbonyl-4-m-(4-ethoxycarbonyl-5-benzyl-2-thiazolylamino)-phenyl-1,4-dihydropyridine 2,6-dimethyl-3,5-dimethoxycarbonyl-4-o-(4-ethoxycarbonylmethyl-2-thiazolylamino)-phenyl-1,4-dihydropyridine, hydrochloride, M.P. 220°–223°

2,6-dimethyl-3,5-dimethoxycarbonyl-4-m-(4-ethoxycarbonylmethyl-2-thiazolylamino)-phenyl-1,4-dihydropyridine 2,6-dimethyl-3,5-dimethoxycarbonyl-4-o-[4-(2-pyridyl)-2-thiazolylamino]-phenyl-1,4-dihydropyridine, M.P. 222°–224° (decomposition); dihydrochloride, M.P. 181°–187° (decomposition)

2,6-dimethyl-3,5-dimethoxycarbonyl-4-o-[4-(2-thienyl)-2-thiazolylamino]-phenyl-1,4-dihydropyridine, M.P. 177°–180° (decomposition)

2,6-dimethyl-3,5-dimethoxycarbonyl-4-o-[4-(3-thienyl)-2-thiazolylamino]-phenyl-14-dihydropyridine, M.P. 192°–194° (decomposition)

2,6-dimethyl-3,5-dimethoxycarbonyl-4-m-[4-(2-pyridyl)-2-thiazolylamino]-phenyl-1,4-dihydropyridine 2,6-dimethyl-3,5-dimethoxycarbonyl-4-o-[4-(3-pyridyl)-2-thiazolylamino]-phenyl-1,4-dihydropyridine, M.P. 253°–256° (decomposition); dihydrochloride, M.P. 183°–192° (decomposition)

2,6-dimethyl-3,5-dimethoxycarbonyl-4-m-[4-(3-pyridyl)-2-thiazolylamino]-phenyl-1,4-dihydropyridine 2,6-dimethyl-3,5-dimethoxycarbonyl-4-o-[4-(4-pyridyl)-2-thiazolylamino]-phenyl-1,4-dihydropyridine, M.P. 248°–251° (decomposition)

2,6-dimethyl-3,5-dimethoxycarbonyl-4-m-[4-(4-pyridyl)-2-thiazolylamino]-phenyl-1,4-dihydropyridine 2,6-dimethyl-3,5-dimethoxycarbonyl-4-o-[4-(3-cyano-6-methyl-2-pyridon-5-yl)-2-thiazolylamino]-phenyl-1,4-dihydropyridine, hydrobromide, M.P. 252°

2,6-dimethyl-3,5-dimethoxycarbonyl-4-m-[4-(3-cyano-6-methyl-2-pyridon-5-yl)-2-thiazolylamino]-phenyl-1,4-dihydropyridine thiazolylamino)-phenyl-1,4-dihydropyridine 2,6-dimethyl-3,5-dimethoxycarbonyl-4-o-(4-phenyl-5-methyl-2-thiazolylamino)-phenyl-1,4-dihydropyridine, hydrobromide, M.P. 236°–237° (decomposition)

2,6-dimethyl-3,5-dimethoxycarbonyl-4-m-(4-phenyl-5-methyl-2-thiazolylamino)-phenyl-1,4-dihydropyridine 2,6-dimethyl-3,5-dimethoxycarbonyl-4-o-(4-o-tolyl-2-thiazolylamino)-phenyl-1,4-dihydropyridine 2,6-dimethyl-3,5-dimethoxycarbonyl-4-m-(4-o-tolyl-2-thiazolylamino)-phenyl-1,4-dihydropyridine 2,6-dimethyl-3,5-dimethoxycarbonyl-4-o-(4-m-tolyl-2-thiazolylamino)-phenyl-1,4-dihydropyridine, hydrobromide, M.P. 179°–182° (decomposition)

2,6-dimethyl-3,5-dimethoxycarbonyl-4-m-(4-m-tolyl-2-thiazolylamino)-phenyl-1,4-dihydropyridine 2,6-dimethyl-3,5-dimethoxycarbonyl-4-o-(4-p-tolyl-2-thiazolylamino)-phenyl-1,4-dihydropyridine, hydrobromide, M.P. 177°–180° (decomposition)

2,6-dimethyl-3,5-dimethoxycarbonyl-4-m-(4-p-tolyl-2-thiazolylamino)-phenyl-1,4-dihydropyridine 2,6-dimethyl-3,5-dimethoxycarbonyl-4-o-[4-(2,4,6-trimethylphenyl)-2-thiazolylamino]-phenyl-1,4-dihydropyridine, hydrobromide, M.P. 187°–188° (decomposition)

2,6-dimethyl-3,5-dimethoxycarbonyl-4-m-[4-(2,4,6-trimethylphenyl)-2-thiazolylamino]-phenyl-1,4-dihydropyridine 2,6-dimethyl-3,5-dimethoxycarbonyl-4-o-[4-(2,6-dimethyl-4-tert.-butylphenyl)-2-thiazolylamino]-phenyl-1,4-dihydropyridine, hydrobromide, M.P. 214° (decomposition)

2,6-dimethyl-3,5-dimethoxycarbonyl-4-m-[4-(2,6-dimethyl-4-tert.-butylphenyl)-2-thiazolylamino]-phenyl-1,4-dihydropyridine 2,6-dimethyl-3,5-dimethoxycarbonyl-4-o-(4-o-methoxyphenyl-2-thiazolylamino)-phenyl-1,4-dihydropyridine 2,6-dimethyl-3,5-dimethoxycarbonyl-4-m-(4-o-methoxyphenyl-2-thiazolylamino)-phenyl-1,4-dihydropyridine 2,6-dimethyl-3,5-dimethoxycarbonyl-4-o-(4-m-methoxyphenyl-2-thiazolylamino)-phenyl-1,4-dihydropyridine 2,6-dimethyl-3,5-dimethoxycarbonyl-4-m-(4-m-methoxyphenyl-2-thiazolylamino)-phenyl-1,4-dihydropyridine 2,6-dimethyl-3,5-dimethoxycarbonyl-4-o-(4-p-methoxyphenyl-2-thiazolylamino)-phenyl-1,4-dihydropyridine, hydrochloride, M.P. 213°-214°; hydrobromide, M.P. 162°-167° (decomposition); methanesulfonate, M.P. 218°-219° (decomposition); sulfate, M.P. 209°-210° (decomposition) hydrobromide, M.P. 162°-167° (decomposition)

2,6-dimethyl-3,5-dimethoxycarbonyl-4-m-(4-p-methoxyphenyl-2-thiazolylamino)-phenyl-1,4-dihydropyridine 2,6-dimethyl-3,5-dimethoxycarbonyl-4-o-[4-(2,5-dimethoxyphenyl)-2-thiazolylamino]-phenyl-1,4-dihydropyridine, hydrobromide, M.P. 207°-210° (decomposition)

2,6-dimethyl-3,5-dimethoxycarbonyl-4-m-[4-(2,5-dimethoxyphenyl)-2-thiazolylamino]-phenyl-1,4-dihydropyridine 2,6-dimethyl-3,5-dimethoxycarbonyl-4-o-[4-(3,4-dimethoxyphenyl)-2-thiazolylamino]-phenyl-1,4-dihydropyridine hydrobromide, M.P. 206°-208° (decomposition)

2,6-dimethyl-3,5-dimethoxycarbonyl-4-m-[4-(3,4-dimethoxyphenyl)-2-thiazolylamino]-phenyl-1,4-dihydropyridine 2,6-dimethyl-3,5-dimethoxycarbonyl-4-o-[4-(3,4-dimethoxyphenyl)-5-methyl-2-thiazolylamino]-phenyl-1,4-dihydropyridine, hydrobromide, M.P. 218°-219° (decomposition)

2,6-dimethyl-3,5-dimethoxycarbonyl-4-m-[4-(3,4-dimethoxyphenyl)-5-methyl-2-thiazolylamino]-phenyl-1,4-dihydropyridine 2,6-dimethyl-3,5-dimethoxycarbonyl-4-o-[4-(3,4,5-trimethoxyphenyl)-2-thiazolylamino]-phenyl-1,4-dihydropyridine, hydrobromide, M.P. 210°-212° (decomposition)

2,6-dimethyl-3,5-dimethoxycarbonyl-4-m-[4-(3,4,5-trimethoxyphenyl)-2-thiazolylamino]-phenyl-1,4-dihydropyridine 2,6-dimethyl-3,5-dimethoxycarbonyl-4-o-(4-p-ethoxyphenyl-2-thiazolylamino)-phenyl-1,4-dihydropyridine, hydrobromide, M.P. 185°-187° (decomposition)

2,6-dimethyl-3,5-dimethoxycarbonyl-4-m-(4-p-ethoxyphenyl-2-thiazolylamino)-phenyl-1,4-dihydropyridine 2,6-dimethyl-3,5-dimethoxycarbonyl-4-o-(4-o-fluorophenyl-2-thiazolylamino)-phenyl-1,4-dihydropyridine 2,6-dimethyl-3,5-dimethoxycarbonyl-4-m-(4-o-fluorophenyl-2-thiazolylamino)-phenyl-1,4-dihydropyridine 2,6-dimethyl-3,5-dimethoxycarbonyl-4-o-(4-m-fluorophenyl-2-thiazolylamino)-phenyl-1,4-dihydropyridine 2,6-dimethyl-3,5-dimethoxycarbonyl-4-m-(4-m-fluorophenyl-2-thiazolylamino)-phenyl-1,4-dihydropyridine 2,6-dimethyl-3,5-dimethoxycarbonyl-4-o-(4-p-fluorophenyl-2-thiazolylamino)-phenyl-1,4-dihydropyridine, hydrobromide, M.P. 184°-186° (decomposition)

2,6-dimethyl-3,5-dimethoxycarbonyl-4-m-(4-p-fluorophenyl-2-thiazolylamino)-phenyl-1,4-dihydropyridine 2,6-dimethyl-3,5-dimethoxycarbonyl-4-o-(4-o-chlorophenyl-2-thiazolylamino)-phenyl-1,4-dihydropyridine, hydrobromide, M.P. 216°-217° (decomposition)

2,6-dimethyl-3,5-dimethoxycarbonyl-4-m-(4-o-chlorophenyl-2-thiazolylamino)-phenyl-1,4-dihydropyridine 2,6-dimethyl-3,5-dimethoxycarbonyl-4-o-(4-m-chlorophenyl-2-thiazolylamino)-phenyl-1,4-dihydropyridine, hydrobromide, M.P. 178°-180° (decomposition)

2,6-dimethyl-3,5-dimethoxycarbonyl-4-m-(4-m-chlorophenyl-2-thiazolylamino)-phenyl-1,4-dihydropyridine 2,6-dimethyl-3,5-dimethoxycarbonyl-4-o-(4-p-chlorophenyl-2-thiazolylamino)-phenyl-1,4-dihydropyridine, hydrobromide, M.P. 173°-175° (decomposition)

2,6-dimethyl-3,5-dimethoxycarbonyl-4-m-(4-p-chlorophenyl-2-thiazolylamino)-phenyl-1,4-dihydropyridine 2,6-dimethyl-3,5-dimethoxycarbonyl-4-o-(4-p-chlorophenyl-5-methyl-2-thiazolylamino)-phenyl-1,4-dihydropyridine, hydrobromide, M.P. 236°-237° (decomposition)

2,6-dimethyl-3,5-dimethoxycarbonyl-4-m-(4-p-chlorophenyl-5-methyl-2-thiazolylamino)-phenyl-1,4-dihydropyridine 2,6-dimethyl-3,5-dimethoxycarbonyl-4-o-[4-(2,4-dichlorophenyl)-2-thiazolylamino]-phenyl-1,4-dihydropyridine, hydrochloride, M.P. 212°-215° (decomposition)

2,6-dimethyl-3,5-dimethoxycarbonyl-4-m-[4-(2,4-dichlorophenyl)-2-thiazolylamino]-phenyl-1,4-dihydropyridine, 2,6-dimethyl-3,5-dimethoxycarbonyl-4-o-[4-(3,4-dichlorophenyl)-2-thiazolylamino]-phenyl-1,4-dihydropyridine hydrobromide, M.P. 195°-197° (decomposition)

2,6-dimethyl-3,5-dimethoxycarbonyl-4-m-[4-(3,4-dichlorophenyl)-2-thiazolylamino]-phenyl-1,4-dihydropyridine 2,6-dimethyl-3,5-dimethoxycarbonyl-4-o-(4-p-bromophenyl- 2-thiazolylamino)-phenyl-1,4-dihydropyridine 2,6-dimethyl-3,5-dimethoxycarbonyl-4-m-(4-p-bromophenyl-2-thiazolylamino)-phenyl-1,4-dihydropyridine 2,6-dimethyl-3,5-dimethoxycarbonyl-4-o-[4-(2,4-dimethoxy-5-bromophenyl)-2-thiazolylamino]-phenyl-1,4-dihydropyridine, hydrobromide, M.P. 245°–246° (decomposition)

2,6-dimethyl-3,5-dimethoxycarbonyl-4-m-[4-(2,4-dimethoxy-5-bromophenyl)-2-thiazolylamino]-phenyl-1,4-dihydropyridine 2,6-dimethyl-3,5-dimethoxycarbonyl-4-o-(4-m-trifluoromethylphenyl-2-thiazolylamino)-phenyl-1,4-dihydropyridine, hydrobromide, M.P. 193°–195° (decomposition)

2,6-dimethyl-3,5-dimethoxycarbonyl-4-m-(4-m-trifluoromethylphenyl-22-thiazolylamino)-phenyl-1,4-dihydropyridine 2,6-dimethyl-3,5-dimethoxycarbonyl-4-o-(4-o-hydroxyphenyl-2-thiazolylamino)-phenyl-1,4-dihydropyridine 2,6-dimethyl-3,5-dimethoxycarbonyl-4-m-(4-o-hydroxyphenyl-2-thiazolylamino)-phenyl-1,4-dihydropyridine 2,6-dimethyl-3,5-dimethoxycarbonyl-4-o-(4-m-hydroxyphenyl-2-thiazolylamino)-phenyl-1,4-dihydropyridine 2,6-dimethyl-3,5-dimethoxycarbonyl-4-m-(4-m-hydroxyphenyl-2-thiazolylamino)-phenyl-1,4-dihydropyridine 2,6-dimethyl-3,5-dimethoxycarbonyl-4-o-(4-p-hydroxyphenyl-2-thiazolylamino)-phenyl-1,4-dihydropyridine, hydrobromide, M.P. 219°–220° (decomposition)

2,6-dimethyl-3,5-dimethoxycarbonyl-4-m-(4-p-hydroxyphenyl-2-thiazolylamino)-phenyl-1,4-dihydropyridine 2,6-dimethyl-3,5-dimethoxycarbonyl-4-o-[4-(3,4-dihydroxyphenyl)-2-thiazolylamino]-phenyl-1,4-dihydropyridine, hydrochloride, M.P. 234°–235° (decomposition)

2,6-dimethyl-3,5-dimethoxycarbonyl-4-m-[4-(3,4-dihydroxyphenyl)-2-thiazolylamino]-phenyl-1,4-dihydropyridine 2,6-dimethyl-3,5-dimethoxycarbonyl-4-o-(4-o-nitrophenyl-2-thiazolylamino)-phenyl-1,4-dihydropyridine, hydrobromide, M.P. 170°–173° (de-composition)

2,6-dimethyl-3,5-dimethoxycarbonyl-4-m-(4-o-nitrophenyl-2-thiazolylamino)-phenyl-1,4-dihydropyridine 2,6-dimethyl-3,5-dimethoxycarbonyl-4-o-(4-m-nitrophenyl-2-thiazolylamino)-phenyl-1,4-dihydropyridine, hydrobromide, M.P. 186°–188° (decomposition)

2,6-dimethyl-3,5-dimethoxycarbonyl-4-m-(4-m-nitrophenyl-2-thiazolylamino)-phenyl-1,4-dihydropyridine 2,6-dimethyl-3,5-dimethoxycarbonyl-4-o-(4-p-nitrophenyl-2-thiazolylamino)-phenyl-1,4-dihydropyridine, hydrobromide, M.P. 177°–179° (decomposition)

2,6-dimethyl-3,5-dimethoxycarbonyl-4-m-(4-p-nitrophenyl-2-thiazolylamino)-phenyl-1,4-dihydropyridine 2,6-dimethyl-3,5-dimethoxycarbonyl-4-o-[4-(3-nitro-4-methoxyphenyl)-2-thiazolylamino]-phenyl-1,4-dihydropyridine, hydrobromide, M.P. 195°–197° (decomposition)

2,6-dimethyl-3,5-dimethoxycarbonyl-4-m-[4-(3-nitro-4-methoxyphenyl)-2-thiazolylamino]-phenyl-1,4-dihydropyridine, 2,6-dimethyl-3,5-dimethoxycarbonyl-4-o-(4-p-dimethylaminophenyl-2-thiazolylamino)-phenyl-1,4-dihydropyridine 2,6-dimethyl-3,5-dimethoxycarbonyl-4-m-(4-p-dimethylaminophenyl-2-thiazolylamino)-phenyl-1,4-dihydropyridine 2,6-dimethyl-3,5-dimethoxycarbonyl-4-o-(4-p-acetamidophenyl-2-thiazolylamino)-phenyl-1,4-dihydropyridine 2,6-dimethyl-3,5-dimethoxycarbonyl-4-m-(4-p-acetamidophenyl-2-thiazolylamino)-phenyl-1,4-dihydropyridine 2,6-dimethyl-3,5-dimethoxycarbonyl-4-o-[4-(3-acetamido-4-methoxyphenyl)-2-thiazolylamino]-phenyl-1,4-dihydropyridine, hydrobromide, M.P. 210° (decomposition)

2,6-dimethyl-3,5-dimethoxycarbonyl-4-m-[4-(3-acetoamido-4-methoxyphenyl)-2-thiazolylamino]-phenyl-1,4-dihydropyridine 2,6-dimethyl-3,5-dimethoxycarbonyl-4-o-(4-p-cyanophenyl-2-thiazolylamino)-phenyl-1,4-dihydropyridine, hydrobromide, M.P. 178°–180° (decomposition)

2,6-dimethyl-3,5-dimethoxycarbonyl-4-m-(4-p-cyanophenyl)-2-thiazolylamino)-phenyl-1,4-dihydropyridine 2,6-dimethyl-3,5-dimethoxycarbonyl-4-o-(4-p-carbamoylphenyl-2-thiazolylamino)-phenyl-1,4-dihydropyridine 2,6-dimethyl-3,5-dimethoxycarbonyl-4-m-(4-p-carbamoylphenyl-2-thiazolylamino)-phenyl-1,4-dihydropyridine 2,6-dimethyl-3,5-dimethoxycarbonyl-4-o-(4-o-sulphamoylphenyl-2-thiazolylamino)-phenyl-1,4-dihydropyridine 2,6-dimethyl-3,5-dimethoxycarbonyl-4-m-(4-o-sulphamoylphenyl-2-thiazolylamino)-phenyl-1,4-dihydropyridine 2,6-dimethyl-3,5-dimethoxycarbonyl-4-o-(4-m-sulphamoylphenyl-2-thiazolylamino)-phenyl-1,4-dihydropyridine, hydrobromide, M.P. 155°–157° (decomposition)

2,6-dimethyl-3,5-dimethoxycarbonyl-4-m-(4-m-sulphamoylphenyl-2-thiazolylamino)-phenyl-1,4-dihydropyridine 2,6-dimethyl-3,5-dimethoxycarbonyl-4-o-(4-p-sulphamoylphenyl-2-thiazolylamino)-phenyl-1,4-dihydropyridine, hydrobromide, M.P. 254°–256° (decomposition)

2,6-dimethyl-3,5-dimethoxycarbonyl-4-m-(4-p-sulphamoylphenyl-2-thiazolylamino)-phenyl-1,4-dihydropyridine 2,6-dimethyl-3,5-dimethoxycarbonyl-4-o-(4-p-difluoromethoxyphenyl-2-thiazolylamino)-phenyl-1,4-dihydropyridine 2,6-dimethyl-3,5-dimethoxycarbonyl-4-m-(4-p-difluoromethoxyphenyl-2-thiazolylamino)-phenyl-1,4-dihydropyridine 2,6-dimethyl-3,5-dimethoxycarbonyl-4-o-[4-(4-diphenylyl)-2-thiazolylamino]-phenyl-1,4-dihydropyridine, hydrobromide, M.P. 184°–189° (decomposition)

2,6-dimethyl-3,5-dimethoxycarbonyl-4-m-[4-(4-diphenylyl)-2-thiazolylamino]-phenyl-1,4-dihydropyridine 2,6-dimethyl-3,5-dimethoxycarbonyl-4-o-(4-p-phenoxyphenyl-2-thiazolylamino)-phenyl-1,4-dihydropyridine 2,6-dimethyl-3,5-dimethoxycarbonyl-4-m-(4-p-phenoxyphenyl-2-thiazolylamino)-phenyl-1,4-dihydropyridine.

EXAMPLE 14

The following 2,6-dimethyl-3,5-diethoxycarbonyl-1,4-dihydropyridines are obtained analogously to Example 13 using 2,6-dimethyl-3,5-diethoxycarbonyl-4-o-thioureidophenyl-1,4-dihydropyridine [M.P. 217°–218° (decomposition); obtainable from 2,6-dimethyl-3,5-diethoxycarbonyl-4-o-aminophenyl-1,4-dihydropyridine via the 4-o-N'-benzoylthioureido derivative (M.P. 184°–186°)] or using 2,6-dimethyl-3,5-diethoxycarbonyl-4-m-thioureidophenyl-1,4-dihydropyridine (M.P. 198°):

2,6-dimethyl-3,5-diethoxycarbonyl-4-o-(2-thiazolylamino)-phenyl-1,4-dihydropyridine 2,6-dimethyl-3,5-diethoxycarbonyl-4-m-(2-thiazolylamino)-phenyl-1,4-dihydropyridine 2,6-dimethyl-3,5-diethoxycarbonyl-4-o-(4-methyl-2-thiazolylamino)-phenyl-1,4-dihydropyridine, hydrochloride, M.P. 179°–183°

2,6-dimethyl-3,5-diethoxycarbonyl-4-m-(4-methyl-2-thiazolylamino)-phenyl-1,4-dihydropyridine, hydrochloride, M.P. 208°–210°

2,6-dimethyl-3,5-diethoxycarbonyl-4-o-(4,5-dimethyl-2-thiazolylamino)-phenyl-1,4-dihydropyridine 2,6-dimethyl-3,5-diethoxycarbonyl-4-m-(4,5-dimethyl-2-thiazolylamino)-phenyl-1,4-dihydropyridine, hydrochloride, M.P. 205°–207°

2,6-dimethyl-3,5-diethoxycarbonyl-4-o-(4-methyl-5-phenyl-2-thiazolylamino)-phenyl-1,4-dihydropyridine, hydrobromide, M.P. 219°–221° (decomposition)

2,6-dimethyl-3,5-diethoxycarbonyl-4-m-(4-methyl-5-phenyl-2-thiazolylamino)-phenyl-1,4-dihydropyridine 2,6-dimethyl-3,5-diethoxycarbonyl-4-o-(4-ethoxycarbonyl-2-thiazolylamino)-phenyl-1,4-dihydropyridine 2,6-dimethyl-3,5-diethoxycarbonyl-4-m-(4-ethoxycarbonyl-2-thiazolylamino)-phenyl-1,4-dihydropyridine, hydrobromide, M.P. 137°–139°

2,6-dimethyl-3,5-diethoxycarbonyl-4-o-(4-ethoxycarbonyl-5-benzyl-2-thiazolylamino)-phenyl-1,4-dihydropyridine, hydrobromide, M.P. 212°–213° (decomposition)

2,6-dimethyl-3,5-diethoxycarbonyl-4-m-(4-ethoxycarbonyl-5-benzyl-2-thiazolylamino)-phenyl-1,4-dihydropyridine 2,6-dimethyl-3,5-diethoxycarbonyl-4-o-(4-ethoxycarbonylmethyl-2-thiazolylamino)-phenyl-1,4-dihydropyridine 2,6-dimethyl-3,5-diethoxycarbonyl-4-m-(4-ethoxycarbonylmethyl)-2-thiazolylamino)-phenyl-1,4-dihydropyridine, hydrochloride, M.P. 192°–193°

2,6-dimethyl-3,5-diethoxycarbonyl-4-o-(4-carbamoyl-2-thiazolylamino)-phenyl-1,4-dihydropyridine 2,6-dimethyl-3,5-diethoxycarbonyl-4-o-(4-N-methylcarbamoyl-2-thiazolylamino)-phenyl-1,4-dihydropyridine 2,6-dimethyl-3,5-diethoxycarbonyl-4-o-(4-N,N-dimethylcarbamoyl-2-thiazolylamino)-phenyl-1,4-dihydropyridine 2,6-dimethyl-3,5-diethoxycarbonyl-4-o-(4-carboxy-2-thiazolyamine)-phenyl- 1,4-dihydropyridine 2,6-dimethyl-3,5-diethoxycarbonyl-4-o-(4-benzyl-2-thiazolylamino)-phenyl-1,4-dihydropyridine 2,6-dimethyl-3,5-diethoxycarbonyl-4-o-[4-(2-(thienyl)-2-thiazolylamino]-phenyl-1,4-dihydropyridine, M.P. 142°–144° (decomposition)

2,6-dimethyl-3,5-diethoxycarbonyl-4-o-[4-(3-thienyl)-2-thiazolylamino]-phenyl-1,4-dihydropyridine, M.P. 140°–144° (decomposition)

2,6-dimethyl-3,5-diethoxycarbonyl-4-o-[4-(2-pyridyl)-2-thiazolylamino]-phenyl-1,4-dihydropyridine, M.P. 165° (decomposition)

2,6-dimethyl-3,5-diethoxycarbonyl-4-m-[4-(2-pyridyl)-2-thiazolylamino]-phenyl-1,4-dihydropyridine 2,6-dimethyl-3,5-diethoxycarbonyl-4-o-[4-(3-pyridyl)-2-thiazolylamino]-phenyl-1,4-dihydropyridine, M.P. 170°–175° (decomposition)

2,6-dimethyl-3,5-diethoxycarbonyl-4-m-[4-(3-pyridyl)-2-thiazolylamino]-phenyl-1,4-dihydropyridine 2,6-dimethyl-3,5-diethoxycarbonyl-4-o-[4-(4-pyridyl)-2-thiazolylamino]-phenyl-1,4-dihydropyridine, M.P. 250°–252° (decomposition); dihydrochloride, M.P. 163°–170° (decomposition)

2,6-dimethyl-3,5-diethoxycarbonyl-4-m-[4-(4-pyridyl)-2-thiazolylamino]-phenyl-1,4-dihydropyridine 2,6-dimethyl-3,5-diethoxycarbonyl-4-o-[4-(3-cyano-6-methyl-2-pyridon-5-yl)-2-thiazolylamino]-phenyl-1,4-dihydropyridine 2,6-dimethyl-3,5-diethoxycarbonyl-4-m-[4-(3-cyano-6-methyl-2-pyridon-5-yl)-2-thiazolylamino]-phenyl-1,4-dihydropyridine, hydrobromide, M.P. 120° (decomposition)

2,6-dimethyl-3,5-diethoxycarbonyl-4-o-(4-phenyl-2-thiazolylamino)-phenyl-1,4-dihydropyridine, hydrobromide, M.P. 243°–245° (decomposition)

2,6-dimethyl-3,5-diethoxycarbonyl-4-m-(4-phenyl-2-thiazolylamino)-phenyl-1,4-dihydropyridine 2,6-dimethyl-3,5-diethoxycarbonyl-4-o-(4-phenyl-5-methyl-2-thiazolylamino)-phenyl-1,4-dihydropyridine, hydrobromide, M.P. 204°–205° (decomposition)

2,6-dimethyl-3,5-diethoxycarbonyl-4-m-(4-phenyl-5-methyl-2-thiazolylamino)-phenyl-1,4-dihydropyridine 2,6-dimethyl-3,5-diethoxycarbonyl-4-o-(4-o-tolyl-2-thiazolylamino)-phenyl-1,4-dihydropyridine 2,6-dimethyl-3,5-diethoxycarbonyl-4-m-(4-o-tolyl-2-thiazolylamino)-phenyl-1,4-dihydropyridine, hydrobromide, M.P. 218°–220° (decomposition)

2,6-dimethyl-3,5-diethoxycarbonyl-4-m-(4-m-tolyl-2-thiazolylamino)-phenyl-1,4-dihydropyridine 2,6-dimethyl-3,5-diethoxycarbonyl-4-o-(4-p-tolyl-2-thiazolylamino)-phenyl-1,4-dihydropyridine, hydrobromide, M.P. 207°–209° (decomposition)

2,6-dimethyl-3,5-diethoxycarbonyl-4-m-(4-p-tolyl-2-thiazolylamino)-phenyl-1,4-dihydropyridine 2,6-dimethyl-3,5-diethoxycarbonyl-4-o-[4-(2,4,6-trimethylphenyl)-2-thiazolylamino]-phenyl-1,4-dihydropyridine, hydrobromide, M.P. 218°–220° (decomposition)

2,6-dimethyl-3,5-diethoxycarbonyl-4-m-[4-(2,4,6-trimethylphenyl)-2-thiazolylamino]-phenyl-1,4-dihydropyridine 2,6-dimethyl-3,5-diethoxycarbonyl-4-o-[4-(2,6-dimethyl-24-tert.-butylphenyl)-2-thiazolylamino]-phenyl-1,4-dihydropyridine, hydrobromide, M.P. 243° (decomposition)

2,6-dimethyl-3,5-diethoxycarbonyl-4-m-[4-(2,6-dimethyl-4-tert.-butylphenyl)-2-thiazolylamino]-phenyl-1,4-dihydropyridine 2,6-dimethyl-3,5-diethoxycarbonyl-4-o-(4-o-methoxyphenyl-2-thiazolylamino)-phenyl-1,4-dihydropyridine 2,6-dimethyl-3,5-diethoxycarbonyl-4-m-(4-o-methoxyphenyl-2-thiazolylamino)-phenyl-1,4-dihydropyridine 2,6-dimethyl-3,5-diethoxycarbonyl-4-o-(4-m-methoxyphenyl-2-thiazolylamino)-phenyl-1,4-dihydropyridine 2,6-dimethyl-3,5-diethoxycarbonyl-4-m-(4-m-methoxyphenyl-2-thiazolylamino)-phenyl-1,4-dihydropyridine 2,6-dimethyl-3,5-diethoxycarbonyl-4-o-(4-p-methoxyphenyl-2-thiazolylamino)-phenyl-1,4-dihydropyridine, M.P. 213°-215° (decomposition); hydrobromide, M.P. 205°-210° (decomposition); hydrochloride, M.P. 227°-229° (decomposition); methanesulfonate, M.P. 202°-203° (decomposition); sulfate, M.P. 194°-196° (decomposition)

2,6-dimethyl-3,5-diethoxycarbonyl-4-m-(4-p-methoxyphenyl-2-thiazolylamino)-phenyl-1,4-dihydropyridine, 2,6-dimethyl-3,5-diethoxycarbonyl-4-o-[4-(2,5-dimethoxyphenyl)-2-thiazolylamino]-phenyl-1,4-dihydrpyridine, hydrobromide, M.P. 209°-210° (decomposition)

2,6-dimethyl-3,5-diethoxycarbonyl-4-m-[4-(2,5-dimethoxyphenyl)-2-thiazolylamino]-phenyl-1,4-dihydropyridine 2,6-dimethyl-3,5-diethoxycarbonyl-4-o-[4-(3,4-dimethoxyphenyl)-2-thiazolylamino]-phenyl-1,4-dihydropyridine, hydrobromide, M.P. 191°-193° (decomposition)

2,6-dimethyl-3,5-diethoxycarbonyl-4-m-[4-(3,4-dimethoxyphenyl)-2-thiazolylamino]-phenyl-1,4-dihydropyridine 2,6-dimethyl-3,5-diethoxycarbonyl-4-o-[4-(3,4-dimethoxyphenyl)-5-methyl-2-thiazolylamino]-phenyl-1,4-dihydropyridine hydrobromide, M.P. 211°-212° (decomposition)

2,6-dimethyl-3,5-diethoxycarbonyl-4-m-[4-(3,4-dimethoxyphenyl)-5-methyl-2-thiazolylamino]-phenyl-1,4-dihydropyridine 2,6-dimethyl-3,5-diethoxycarbonyl-4-o-[4-(3,4,5-trimethoxyphenyl)-2-thiazolylamino]-phenyl-1,4-dihydropyridine, hydrobromide, M.P. 217°-218° (decomposition)

2,6-dimethyl-3,5-diethoxycarbonyl-4-m-[4-(3,4,5-trimethoxyphenyl)-2-thiazolylamino]-phenyl-1,4-dihydropyridine 2,6-dimethyl-3,5-diethoxycarbonyl-4-o-(4-p-ethoxyphenyl-2-thiazolylamino)-phenyl-1,4-dihydropyridine, hydrobromide, M.P. 208°-°210° (decomposition)

2,6-dimethyl-3,5-diethoxycarbonyl-4-m-(4-p-ethoxyphenyl-2-thiazolylamino)-phenyl-1,4-dihydropyridine 2,6-dimethyl-3,5-diethoxycarbonyl-4-o-(4-p-methylthiophenyl-2-thiazolylamino)-phenyl-1,4-dihydropyridine 2,6-dimethyl-3,5-diethoxycarbonyl-4-o-(4-p-methylsulphinylphenyl-2-thiazolylamino)-phenyl-1,4-dihydropyridine 2,6-dimethyl-3,5-diethoxycarbonyl-4-o-(4-p-methylsulphonylphenyl-2-thiazolylamino)-phenyl-1,4-dihydropyridine 2,6-dimethyl-3,5-diethoxycarbonyl-4-o-(4-o-fluorophenyl-2-thiazolylamino)-pheny-1,4-dihydropyridine 2,6-dimethyl-3,5-diethoxycarbonyl-4-m-(4-o-fluorophenyl-2-thiazolylamino)-phenyl-1,4-dihydropyridine 2,6-dimethyl-3,5-diethoxycarbonyl-4-o-(4-m-fluorophenyl-2-thiazolylamino)-phenyl-1,4-dihydropyridine 2,6-dimethyl-3,5-diethoxycarbonyl-4-m-(4-m-fluorophenyl-2-thiazolylamino)-phenyl-1,4-dihydropyridine 2,6-dimethyl-3,5-diethoxycarbonyl-4-o-(4-p-fluorophenyl-2-thiazolylamino)-phenyl-1,4-dihydropyridine, hydrobromide, M.P. 242°-244° (decomposition)

2,6-dimethyl-3,5-diethoxycarbonyl-4-m-(4-p-fluorophenyl-2-thiazolylamino)-phenyl-1,4-dihydropyridine 2,6-dimethyl-3,5-diethoxycarbonyl-4-o-(4-o-chlorophenyl-2-thiazolylamino)-phenyl-1,4-dihydropyridine, hydrobromide, M.P. 217°-218° (decomposition)

2,6-dimethyl-3,5-diethoxycarbonyl-4-m-(4-o-chlorophenyl-2-thiazolylamino)-phenyl-1,4-dihydropyridine 2,6-dimethyl-3,5-diethoxycarbonyl-4-o-(4-m-chlorophenyl-2-thiazolylamino)-phenyl-1,4-dihydropyridine, hydrobromide M.P. 204°-206° (decomposition)

2,6-dimethyl-3,5-diethoxycarbonyl-4-m-(4-m-chlorophenyl-2-thiazolylamino)-phenyl-1,4-dihydropyridine 2,6-dimethyl-3,5-diethoxycarbonyl-4-o-(4-p-chlorophenyl-2-thiazolylamino)-phenyl-1,4-dihydropyridine, hydrobromide, M.P. 200°-203° (decomposition)

2,6-dimethyl-3,5-diethoxycarbonyl-4-m-(4-p-chlorophenyl-2-thiazolylamino)-phenyl-1,4-dihydropyridine 2,6-dimethyl-3,5-diethoxycarbonyl-4-o-(4-p-chlorophenyl-5-methyl-2-thiazolylamino)-phenyl-1,4-dihydropyridine, hydrobromide, M.P. 200°-201° (decomposition)

2,6-dimethyl-3,5-diethoxycarbonyl-4-m-(4-p-chlorophenyl-5-methyl-2-thiazolylamino)-phenyl-1,4-dihydropyridne 2,6-dimethyl-3,5-diethoxycarbonyl-4-o-[4-(2,4-dichlorophenyl)-2-thiazolylamino]-phenyl-1,4-dihydropyridine, hydrochloride, M.P. 220°-223° (decomposition)

2,6-dimethyl-3,5-diethoxycarbonyl-4-m-[4-(2,4-dichlorophenyl)-2-thiazolylamino]-phenyl-1,4-dihydropyridine, 2,6-dimethyl-3,5-diethoxycarbonyl-4-o-[4-(3,4-dichlorophenyl)-2-thiazolylamino]-phenyl-1,4-dihydropyridine, hydrobromide, M.P. 205°-209° (decomposition)

2,6-dimethyl-3,5-diethoxycarbonyl-4-m-[4-(3,4-dichlorophenyl)-2-thiazolylamino]-phenyl-1,4-dihydropyridine 2,6-dimethyl-3,5-diethoxycarbonyl-4-o-(4-p-bromophenyl2-thiazolylamino)-phenyl-1,4-dihydropyridine 2,6-dimethyl-3,5-diethoxycarbonyl-4-m-(4-p-bromophenyl-2-thiazolylamino)-phenyl-1,4-dihydropyridine 2,6-dimethyl-3,5-diethoxycarbonyl-4-o-[4-(2,4-dimethoxy-5-bromophenyl)-2-thiazolylamino]-phenyl-1,4-dihydropyridine, hydrobromide, M.P. 216°-218° (decomposition)

2,6-dimethyl-3,5-diethoxycarbonyl-4-m-[4-(2,4-dimethoxy-5-bromophenyl)-2-thiazolylamino]-phenyl-1,4-dihydropyridine 2,6-dimethyl-3,5-diethoxycarbonyl-4-o-(4-p-iodophenyl- -thiazolylamino)-phenyl-1,4-dihydropyridine 2,6-dimethyl-3,5-diethoxycarbonyl-4-o-(4-m-trifluoromethylphenyl-2-thiazolylamino)-phenyl-1,4-dihydropyridine, hydrobromide, M.P. 205° (decomposition)

2,6-dimethyl-3,5-diethoxycarbonyl-4-m-(4-m-trifluoromethylphenyl-2-thiazolylamino)-phenyl-1,4-dihydropyridine 2,6-dimethyl-3,5-diethoxycarbonyl-4-o-(4-o-hydroxyphenyl-2-thiazolylamino)-phenyl-1,4-dihydropyridine 2,6-dimethyl-3,5-diethoxycarbonyl-4-m-(4-o-hydroxyphenyl-2-thiazolylamino)-phenyl-1,4-dihydropyridine 2,6-dimethyl-3,5-diethoxycarbonyl-4-o-(4-m-hydroxyphenyl-2-thiazolylamino)-phenyl-1,4-dihydropyridine 2,6-dimethyl-3,5-diethoxycarbonyl-4-m-(4-m-hydroxyphenyl-2-thiazolylamino)-phenyl-1,4-dihydropyridine 2,6-dimethyl-3,5-diethoxycarbonyl-4-o-(4-p-hydroxyphenyl-2-thiazolylamino)-phenyl-1,4-dihydropyridine, hydrobromide, M.P. 193°–194° (decomposition)

2,6-dimethyl-3,5-diethoxycarbonyl-4-m-(4-p-hydroxyphenyl-2-thiazolylamino)-phenyl-1,4-dihydropyridine 2,6-dimethyl-3,5-diethoxycarbonyl-4-o-[4-(3,4-dihydroxyphenyl)-2-thiazolylamino]-phenyl-1,4-dihydropyridine, hydrochloride, M.P. 198°–202° (decomposition)

2,6-dimethyl-3,5-diethoxycarbonyl-4-m-[4-(3,4-dihydroxyphenyl)-2-thiazolylamino]-phenyl-1,4-dihydropyridine 2,6-dimethyl-3,5-diethoxycarbonyl-4-o-(4-o-nitrophenyl-2-thiazolylamino)-phenyl-1,4-dihydropyridine, hydrobromide, M.P. 188°–190° (decomposition)

2,6-dimethyl-3,5-diethoxycarbonyl-4-m-(4-o-nitrophenyl-2-thiazolylamino)-phenyl-1,4-dihydropyridine 2,6-dimethyl-3,5-diethoxycarbonyl-4-o-(4-m-nitrophenyl-2-thiazolylamino)-phenyl-1,4-dihydropyridine, hydrobromide, M.P. 190°–191° (decomposition)

2,6-dimethyl-3,5-diethoxycarbonyl-4-m-(4-m-nitrophenyl-2-thiazolylamino)-phenyl-1,4-dihydropyridine 2,6-dimethyl-3,5-diethoxycarbonyl-4-o-(4-p-nitrophenyl-2-thiazolylamino)-phenyl-1,4-dihydropyridine, hydrobromide, M.P. 191°–192° (decomposition)

2,6-dimethyl-3,5-diethoxycarbonyl-4-m-(4-p-nitrophenyl-2-thiazolylamino)-phenyl-1,4-dihydropyridine 2,6-dimethyl-3,5-diethoxycarbonyl-4-o-[4-(3-nitro-4-methoxyphenyl)-2-thiazolylamino]-phenyl-1,4-dihydropyridine, hydrobromide, M.P. 215°–217°

2,6-dimethyl-3,5-diethoxycarbonyl-4-m-[4-(3-nitro-4-methoxyphenyl)-2-thiazolylamino]-phenyl-1,4-dihydropyridine 2,6-dimethyl-3,5-diethoxycarbonyl-4-o-(4-p-dimethylaminophenyl-2-thiazolylamino)-phenyl-1,4-dihydropyridine 2,6-dimethyl-3,5-diethoxycarbonyl-4-m-(4-p-dimethylaminophenyl-2-thiazolylamino)-phenyl-1,4-dihydropyridine 2,6-dimethyl-3,5-diethoxycarbonyl-4-o-(4-p-acetoamidophenyl-2-thiazolylamino)-phenyl-1,4-dihydropyridine 2,6-dimethyl-3,5-diethoxycarbonyl-4-m-(4-p-acetoamidophenyl-2-thiazolylamino)-phenyl-1-4-dihydropyridine 2,6-dimethyl-3,5-diethoxycarbonyl-4-o-[4-(3-acetoamido-4-methoxyphenyl)-2-thiazolylamino]-phenyl-1,4-dihydropyridine, hydrobromide, M.P. 230° (decomposition)

2,6-dimethyl-3,5-diethoxycarbonyl-4-m-[4-(3-acetoamido-4-methoxyphenyl)-2-thiazolylamino]-phenyl-1,4-dihydropyridine 2,6-dimethyl-3,5-diethoxycarbonyl-4-o-(4-p-cyanophenyl-2-thiazolylamino)-phenyl-1,4-dihydropyridine, hydropyridine, hydrobromide M.P. 198°14 200° (decomposition)

2,6-dimethyl-3,5-diethoxycarbonyl-4-m-(4-p-cyanophenyl-2-thiazolylamino)-phenyl-1,4-dihydropyridine, hydrobromide, 2,6-dimethyl-3,5-diethoxycarbonyl-4-o-(4-p-carbamoylphenyl-2-thiazolylamino)=phenyl-1,4-dihydropyridine 2,6-dimethyl-3,5-diethoxycarbonyl-4-m-(4-p-carbamoylphenyl-2-thiazolylamino)-phenyl-1,4-dihydropyridine 2,6-dimethyl-3,5-diethoxycarbonyl-4-o-(4-o-sulphamoylphenyl-2-thiazolylamino)-phenyl-1-4-dihydropyridine 2,6-dimethyl-3,5-diethoxycarbonyl-4-m-(4-o-sulphamoylphenyl-2-thiazolylamino)-phenyl-1,4-dihydropyridine 2,6-dimethyl-3,5-diethoxycarbonyl-4-o-(4-m-sulphamoylphenyl-2-thiazolylamino)-phenyl-1,4-dihydropyridine, hydrobromide, M.P. 211°–212° (decomposition)

2,6-dimethyl-3,5-diethoxycarbonyl-4-m-(4-m-sulphamoylphenyl-2-thiazolylamino)-phenyl-1,4-dihydropyridine 2,6-dimethyl-3,5-diethoxycarbonyl-4-o-(4-p-sulphamoylphenyl- 2-thiazolylamino)-phenyl-1-4-dihydropyridine, hydrobromide, M.P. 248°–250° (decomposition)

2,6-dimethyl-3,5-diethoxycarbonyl-4-m-(4-p-sulphamoylphenyl-2-thiazolylamino)-phenyl-1,4-dihydropyridine 2,6-dimethyl-3,5-diethoxycarbonyl-4-o-(4-p-difluoromethoxyphenyl-2-thiazolylamino)-phenyl-1,4-dihydropyridine 2,6-dimethyl-3,5-diethoxycarbonyl-4-m-(4-p-difluoromethoxyphenyl-2-thiazolylamino)-phenyl-1,4-dihydropyridine 2,6-dimethyl-3,5-diethoxycarbonyl-4-o-[4-(4-diphenylyl)-2-thiazolylamino]-phenyl-1,4-dihydropyridine, hydrobromide, M.P. 206°–209° (decomposition)

2,6-dimethyl-3,5-diethoxycarbonyl-4-m-[4-(4-diphenylyl)-2-thiazolylamino]-phenyl-1,4-dihydropyridine 2,6-dimethyl-3,5-diethoxycarbonyl-4-o-(4-p-phenoxyphenyl-2-thiazolylamino)-phenyl-1-4-dihydropyridine 2,6-dimethyl-3,5-diethoxycarbonyl-4-m-(4-p-phenoxyphenyl-2-thiazolylamino)-phenyl-1,4-dihydropyridine

EXAMPLE 15

A mixture of 4.3 g of 2,6-dimethyl-3,5-dimethoxycarbonyl-4-o-(N'-dimethylaminomethylenethioureido)-phenyl-1,4-dihydropyridine [M.P. 208°–°209° (decomposition); obtainable by boiling 2,6-dimethyl-3,5-dimethoxycarbonyl-4-o-thioureidophenyl-1,4-dihydropyridine and N,N-dimethylformamide dimethyl acetal in acetonitrile for 1.5 hours], 1.26 g of benzyl chloride, 0.6 g of NaH (80%) and 30 ml of DMF is stirred at 20° for 3 hours. After the mixture has been evaporated, water is added and the 2,6-dimethyl-3,5-dimethoxycarbonyl-4-o-(5-phenyl-2-thiazolylamino)-phenyl-1,4-dihydropyridine obtained is filtered off and washed with water.

EXAMPLE 16

A mixture of 572 mg of 2,6-dimethyl-3,5-dimethoxycarbonyl-4-o-(4-p-hydroxyphenyl-2-thiazolylamino)-phenyl-1,4-dihydropyridine hydrobromide, 140 mg of 2-dimethylaminoethyl chloride hydrochloride, 560 mg of $K_2CO_3$, 40 mg of tetrabutylammoium iodide and 20 ml of acetonitrile is stirred at 20° for 24 hours. The precipitated 2,6-dimethyl-3,5-dimethoxycarbonyl-4-o-[4-p-(2-dimethylaminoethoxy)-phenyl-2-thiazolylamino]-phenyl-1,4-dihydropyridine is filtered off with suction and washed with water.

EXAMPLE 17

0.45 g of 80% NaH is added to a solution of 4.88 g of 2,6-dimethyl-3,5-diethoxycarbonyl-4-o-(4-phenyl-2-thiazolyl)-phenyl-1,4-dihydropyridine in 45 ml of DMF. After the mixture has been stirred for half an hour, 1.5 g of 1-(2-chloroethyl)-morpholine in 10 ml of DMF are added and stirring is continued for a further 4 hours at 20°. Working up in the customary manner (ethyl acetate) gives 1-(2-morpholinoethyl)-2,6-dimethyl-3,5-diethoxycarbonyl-4-o-(4-phenyl-2-thiazolyl)-phenyl-1,4-dihydrioyridine.

EXAMPLE 18

A solution of 0.5 g of 2,6-dimethyl-3,5-diethoxycarbonyl-4-o-(4-p-nitrophenyl-2-thiazolyl)-phenyl-1,4-dihydropyridine in 50 ml of methanol is hydrogenated over 0.5 g of Raney nickel under 1 bar and at 20° until absorption ceases. The mixture is filtered and the filtrate is evaporated to give 2,6-dimethyl-3,5-diethoxycarbonyl-4-o-(4-p-aminophenyl-2-thiazolylphenyl)-1,4-dihydropyridine.

The following 2,6-dimethyl-3,5-diethoxycarbonyl-1,4-dihydropyridines are obtained analogously from the corresponding nitro derivatives:

2,6-dimethyl-3,5-diethoxycarbonyl-4-o-(4-o-aminophenyl-2-thiazolyl)-phenyl-1,4-dihydropyridine
2,6-dimethyl-3,5-diethoxycarbonyl-4-m-(4-o-aminophenyl-2-thiazolyl)-phenyl-1,4-dihydropyridine
2,6-dimethyl-3,5-diethoxycarbonyl-4-o-(4-m-aminophenyl-2-thiazolyl)-phenyl-1,4-dihydropyridine
2,6-dimethyl-3,5-diethoxycarbonyl-4-m-(4-m-aminophenyl-2-thiazolyl)-phenyl-1,4-dihydropyridine
2,6-dimethyl-3,5-diethoxycarbonyl-4-m-(4-p-aminophenyl-2-thiazolyl)-phenyl-1,4-dihydropyridine
1,6-dimethyl-3,5-diethoxycarbonyl-4-m-(4-p-aminophenyl-2-thiazolyl)-phenyl-1,4-dihydropyridine

EXAMPLE 19

(a) 1.4 ml of pyridine and 3.84 g of pyridinium bromide perbromide are added at 0°-5° to a solution of 5.03 g of 2,6-dimethyl-3,5-diethoxycarbonyl-4-o-(4-phenyl-2-thiazolylamino)-phenyl-1,4-dihydropyridine in 150 ml of methylene dichloride. The mixture is stirred for 3 hours at 4° and worked up in the customary manner to give 2-bromomethyl-3,5-diethoxycarbonyl-4-o-(4-phenyl-2-thiazolylamino)-phenyl-6-methyl-1,4 -dihydropyridine.

(b) A solution of 0.56 g of the bromine compound obtained in accordance with a) in 30 ml of acetonitrile is boiled for 45 minutes. Evaporation and purification by chromatography give 2-methyl-3-ethoxycarbonyl-4-o-(4-phenyl-2-thiazolylamino)-phenyl-5-oxo-1,4,5,7-tetrahydrofuro[3,4-b]pyridine and 2-hydroxymethyl-3,5-diethoxycarbonyl-4-o-(4-phenyl-2-thiazolylamino)phenyl-6-methyl-1,4-dihydropyridine.

EXAMPLE 20

A solution of 6.49 g of 2-(2-phthalimidoethoxymethyl)-3,5-dimethoxycarbonyl-4-o-(4-phenyl-2-thiazolyl)pphenyl-6-methyl-1,4-dihydropyridine [obtainable from methyl 3-oxo-4-(2-phthalimidoethoxy)-butanoate, 2-(o-formylphenyl)-4-phenylthiazole and methyl 3-aminocrotonate ] and 0.6 g of hydrazine hydrate in 80 ml of ethanol is stirred for 3 hours at 20° and is concentrated. The precipitated 2-(2-o-hydrazinocarbonylbenzamido-ethoxymethyl)-3,5 -dimethoxycarbonyl-4-o-(4-phenyl-2-thiazoly)phenyl-6-methyl-1,4-dihydropyridine is then boiled with 100 ml of methanolic HCl for 1 hour. The mixture is evaporated, the residue is dissolved in 50% ethanol, and the solution is filtered, rendered alkaline to pH 9 and worked up in the customary manner. This gives 2-(2-aminoethoxymethyl)-3,5-dimethoxycarbonyl-4-o-(4-phenyl-2-thiazolyl)-phenyl-6-methyl-1,4-dihydropyridine.

EXAMPLE 21

In analogy to Example 13, 2-methyl-3-methoxycarbonyl-4-o-(4-phenyl-2-thiazolylamino)-phenyl-5-oxo-1,4,5,7-tetrahydrofuro [3,4-b]pyridine [hydrochloride, M.P. 221° (decomposition)] is obtained from 2-methyl-3-methoxycarbonyl-4-o-thioureidophenyl-5-oxo-1,4,5,7-tetrahydrofuro[3,4-b]pyridine [M.P. 217°–219°]; obtainable by hydrogenation of 2-methyl-3-methoxycarbonyl-4-o-nitrophenyl-5-oxo-1,4,5,7-tetrahydrofuro[3,4-b]pyridine on Pd-C in DMF to yield the 4-o-aminophenyl compound (M.P. 183°–184°), reaction with benzoyl isothiocyanate in acetone at 20° to give the 4-o-(N'-benzoylthioureido)phenyl compound (M.P. 170°–174°) and splitting off the benzoyl group ] and 2'-chloroacetophenone.

Analogously, the following 2-methyl-3-methoxycarbonyl-5-oxo-1,4,5,7-tetrahydrofuro[3,4-b]pyridines are obtained:

4-o-(4-methyl-2-thiazolylamino)-phenyl-, hydrochloride, M.P 180°–181° (decomposition)
4-o-(4-ethoxycarbonyl-2-thiazolylamino)-phenyl-, hydrobromide, M.P. 230°–231° (decomposition)
4-o-[4-(2-thienyl)-2-thiazolylamino]-phenyl-, hydrobromide, M.P. 219°–°220° (decomposition)
4-o-[4-(3-thienyl)-2-thiazolylamino]-phenyl-, hydrobromide, M.P. 238°14 240° (decomposition)
4-o-(4-m-tolyl-2-thiazolylamino)-phenyl-, hydrobromide, M.P. 218°–219° (decomposition)
4-o-(4-p-tolyl-2-thiazolylamino)-phenyl-, hydrobromide, M.P. 237°–239° (decomposition)
4-o-(4-m-methoxyphenyl-2-thiazolylamino)-phenyl-, hydrobromide, M.P. 218°–219° (decomposition)
4-o-(4-p-methoxyphenyl-2-thiazolylamino)-phenyl-, hydrochloride, M.P. 233°–234° (decomposition)
4-o-(4-p-fluorophenyl-2-thiazolylamino)-phenyl-, hydrobromide, M.P. 227°–228° (decomposition)
4-o-(4-o-chlorophenyl-2-thiazolylamino)-phenyl-, hydrobromide, M.P. 223°–224° (decomposition)
4-o-(4-m-chlorophenyl-2-thiazolylamino)-phenyl-, hydrobromide, M.P. 209°–211° (decomposition)
4-o-(4-p-chlorophenyl-2-thiazolylamino)-phenyl-, hydrobromide, M.P. 227°–229° (decomposition).

EXAMPLE 22

Analogously to Example 13, 1,7-dioxo-8-o-(4-phenyl-2-thiazolylamino)-phenyl-1,3,4,5,7,8-hexahydrodifuro[3,4-b:3',4'-e]pyridine [hydrochloride, M.P. 264°–268° (decompostion)] is obtained from 1,7-dioxo-8-o-thioureidophenyl-1,3,4,5,7,8-hexahydrodifuro 8 3,4-b: 3',4'-e]pyridine [M.P. 229°–230° (decomposition); obtainable by bromination of 2-methyl-3-methoxycarbonyl-4-o-nitrophenyl-5-oxo-1,4,5,7-tetrahydrofuro[3,4-b]pyridine with pyridinium-hydrobromide-perbromide/triethylamine in THF to yield the 2-bromomethyl compound, cyclization in acetonitrile at 82° to yield 1,7-dioxo-8-o-nitrophenyl-1,3,4,5,7,8-hexahydro-difuro[3,4-b: 3',4'-e]pyridine (M.P. 273°–274°), hydrogenation to yield the 8-o-aminophenyl compound [M.P. 285°–287° (decomposition)], reaction with benzoyl isothiocyanate to yield the 8-o-(N'-benzoylthioureido)-phenyl compound [M.P. 219°–220° (decomposition)] and splitting off the benzoyl group].

Analogously, the,following 1,7-dioxo-1,3,4,5,7,8-hexahydro-difuro[3,4-b: 3',4'-e]pyridines are obtained: 8-o-[4-(2-thienyl)-2-thiazolylamino]-phenyl-, hydrobromide, M.P. 263°–265° (decomposition) 8-o-[4-(3-thienyl)-2-thiazolylamino]-phenyl-, hydrobromide, M.P. 295°–297° (decomposition)

8-o-(4-m-tolyl-2-thiazolylamino)-phenyl-, M.P. 220° (decomposition)

8-o-(4-p-tolyl-2-thiazolylamino)-phenyl-, hydrobromide, M.P. 226°–229° (decomposition)

8-o-(4-m-methoxyphenyl-2-thiazolylamino)-phenyl-, hydrobromide, M.P. 236°–239° (decomposition)

8-o-(4-p-methoxy phenyl-2-thiazolylamino)-phenyl-, hydrochloride, M.P. 239° (decomposition)

8-o-(4-p-fluorophenyl-2-thiazolylamino)-phenyl-, hydrobromide, M.P. 274°–275° (decomposition)

8-o-(4-o-chlorophenyl-2-thiazolylamino(-phenyl-, hydrobromide, M.P. 277° (decomposition)

8-o-(4-m-chlorophenyl-2-thiazolylamino)-phenyl-, hydrobromide, M.P. 268°14 270° (decomposition)

8-o-(4-p-chlorophenyl-2-thiazolylamino)-phenyl-, hydrobromide, M.P. 285°–286° (decomposition).

EXAMPLE 23

A mixture of 0.44 g of 1,7-dioxo-8-o-(4-phenyl-2-thiazolyl-amino)-phenyl-1,3,4,5,7,8-hexahydro-difuro[3,4-b:3',4'-e]-pyridine, 0.25 ml of benzyl bromide, 0.69 g of $K_2CO_3$, 2 ml of DMF and 15 ml of THF is stirred for 8 hours at 20°. After filtration evaporation and chromatography of the resinous residue on silica gel with ethyl acetate, there is obtained 4-benzyl-1,7-dioxo-8-o-(4-phenyl-2-thiazolylamino)-phenyl-1,3,4,5,7,8-hexahydro-difuro[3,4-b:3',4'-e]pyridine, M.P. 162°–165° (decomposition).

The examples below relate to pharmaceutical formulations containing compounds of the formula I or physiologically acceptable salts thereof:

EXAMPLE A: TABLETS

A mixture of 1 kg of 2,6-dimethyl-3,5-diethoxycarbonyl-4-o-(4-p-chlorophenyl-2-thiazolylamino)-phenyl-1,4-dihydropyridine hydrobromide, 4 kg of lactose, 1.2 kg of potato starch, 0.2 kg of talc and 0.1 kg of magnesium stearate is compressed in a customary manner to give tablets in such a way that each tablet contains 5 mg of active compound.

EXAMPLE B: COATED TABLETS

Tablets are compressed analogously to Example A and are then coated in a customary manner with a coating consisting of sucrose, potato starch, talc, tragacanth and a dyestuff.

EXAMPLE C: CAPSULES 10 kg of 2,6-dimethyl-3,5-dimethoxycarbonyl-4-o-(4-phenyl-2-thiazolylamino)-phenyl-1,4-dihydropyridine hydrochloride are filled in a customary manner into hard gelatine capsules in such a way that each capsule contains 50 mg of active compound.

EXAMPLE D: AMPOULES

A mixture of 0.1 kg of 2,6-dimethyl-3,5-dimethoxycarbonyl-4-o-(4-p-fluorophenyl-2-thiazolylamino)-phenyl-1,4-dihydropyridine hydrobromide, 0.27 kg of sodium chloride and 30 l of polyethylene glycol 400 is made up to 100 l with water, the solution is filtered under sterile conditions and filled into ampoules, and the latter are closed in a sterile manner. Each ampoule contains 2 mg of active compound.

Tablets, coated tablets, capsules or ampoules containing one or more of the other active compounds of the formula I and/or physiologically acceptable salts thereof are obtainable analogously.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:
1. A compound of the formula

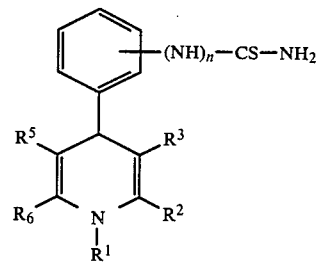

VI wherein
n is 0 or 1
$R^1$ is H, A, Ar-alkyl, AO-alkyl, ArO-alkyl, Ar-alkyl-O-alkyl or $R^7R^8$N-alkyl,
each of $R^2$ and $R^6$ is H, A, Ar-alkyl, Hal-alkyl, $CF_3$, $R^9OCH_2$—, $R^7R^8N$—$(CH_2)_a$—$CHR^{10}$,$R^{11}SO_m$—$CH_2$—, CN or a free CHO group,
each of $R^3$ and $R^5$ is $R^{12}CO$—, $R^{11}SO_2$, $(AO)_2PO$—, $NO_2$ or CN,
$R^7$ is H, A, Ar, AOOC—, Ar-alkyl-OOC, $R^{10}$NHCO—, $R^{11}SO_2$— or Ac,
$R^8$ is H, A or Ar-alkyl,
$R^7$ and $R^8$ together can also be Z, —$COCH_2CH_2CO$—, —COCH=CHCO—or —CO—(o-$C_6H_4$)—CO—,
$R^9$ is H, A, Ar, Ar-alkyl, AO-alkyl, $R^7R^8$N-alkyl, Ac, $R^{10}$NHCO—, $R^{11}SO_2$— or $CF_3SO_2$—,
$R^{10}$ is H, A or Ar,
$R^7$ and $R^{10}$ together can also be alkylene having 2–4 C atoms,
$R^{11}$ is A or Ar, $R^{12}$ is HO, AO, $R^{14}$-alkyl—O—, Z=CH—O—,A, Ar, Het, $R^7R^8$N— or $R^{15}$O-alkyl—NH—, $R^9$ and $R^{12}$ and $R^8$ and $R^{12}$ together in each case can also be a bond, $R^{14}$ is AO, Aro, Ar-alkyl—O—, $R^7R^8$N—, $R^{11}$SO2$^O$— or (AO)2PO—O—, $R^{15}$ is H, A, Ar or Ac, each of a and m are 0, 1 or 2, A is a linear or branched, saturated or unsaturated, aliphatic or cycloaliphatic hydrocarbon radical having 1–20 C atoms, Ac is $R^{10}$CO—, Ar-alkyl—CO— or Ar-alkenyl—CO—, Ar is phenyl; phenyl which is monosubstituted to trisubstituted by A, AO, AcO, Hal, CF3, HO, O2$^N$, H2N, ANH, A2$^N$, AcNH, AOOCNH—, Ar-alkyl—OOCNH—, CN, H2NCO, HOOC, AOOC, H2NSO2 and/or $R^{11}$NHCONH—; or naphthyl, Hal is F, CL, Br or I, Het is a 5-membered or 6-membered, mononuclear or polynuclear, heterocyclic radical which has 1–4 O, N and/or S atoms and which can be monosubstituted or polysubstituted by A, AO, Hal, CF3, HO, O2N, H2N, NHA, NA2, AcNH, ASO$_m$, AOOC, CN, H2NCO, HOOC, H2NSO2, ASO2NH, Ar, Ar-alkenyl and/or pyridyl, and Z is an alkylene chain which has 4 or 5 C atoms and which can be interrupted by O, HN, AN, ArN, Ar-alkyl-N, Ar2CHN or AcN, and alkyl or alkenyl are alkylene or alkenylene chains each of which has 1–4 C atoms.

2. A compound of claim 1, wherein said substituted or unsubstituted Het radical is 1,4-dihydro-4-pyridyl.

* * * * *